US007592147B2

(12) United States Patent
Glimcher et al.

(10) Patent No.: US 7,592,147 B2
(45) Date of Patent: Sep. 22, 2009

(54) MODULATION OF IL-2 PRODUCTION BY T-BET

(75) Inventors: Laurie H. Glimcher, West Newton, MA (US); Eun Sook Hwang, Seoul (KR)

(73) Assignee: President and Fellows of Harvard University, Cambridge, MA (US)

( * ) Notice: Subject to any disclaimer, the term of this patent is extended or adjusted under 35 U.S.C. 154(b) by 101 days.

(21) Appl. No.: 11/593,811

(22) Filed: Nov. 7, 2006

(65) Prior Publication Data
US 2007/0128661 A1 Jun. 7, 2007

Related U.S. Application Data

(60) Provisional application No. 60/734,324, filed on Nov. 7, 2005.

(51) Int. Cl.
*G01N 33/53* (2006.01)
*G01N 33/567* (2006.01)
*C40B 30/04* (2006.01)

(52) U.S. Cl. .............................. 435/7.1; 435/7.2; 506/9

(58) Field of Classification Search ....................... None
See application file for complete search history.

(56) References Cited

U.S. PATENT DOCUMENTS

| 7,365,169 | B2 | 4/2008 | Glimcher et al. |
| 2003/0104528 | A1 | 6/2003 | Glimcher et al. |
| 2003/0186377 | A1 | 10/2003 | Glimcher et al. |
| 2005/0186568 | A1 | 8/2005 | Bandman et al. |
| 2006/0084118 | A1 | 4/2006 | Glimcher et al. |
| 2006/0223116 | A1 | 10/2006 | Glimcher et al. |

FOREIGN PATENT DOCUMENTS

WO   WO-03/048379 A1   6/2003

OTHER PUBLICATIONS

Alcaide, Pilar et al., "Dendritic cell expression of the transcription factor T-bet regulates mast cell progenitor homing to mucosal tissue," *The Journal of Experimental Medicine*, vol. 204(2):431-439 (2007).
Aliprantis, Antonios O. et al., "Transcription factor T-bet regulates skin sclerosis through its function in innate immunity and via IL-13," *PNAS*, vol. 104(8):2827-2830 (2007).
Bettelli, Estelle et al., "Loss of T-bet, But Not STAT1, Prevents the Development of Experimental Autoimmune Encephalomyelitis," *J. Exp. Med.*, vol. 200(1):79-87 (2004).
Buono, Chiara et al., "T-bet deficiency reduces atherosclerosis and alters plaque antigen-specific immune responses," *PNAS*, vol. 102(5):1596-1601 (2005).
Dorfman, David M. et al., "Differential Expression of T-bet, a T-box Transcription Factor Required for Th1 T-Cell Development, in Peripheral T-Cell Lymphomas," *Am. J. Clin. Pathol.*, vol. 120(6):866-873 (2003).
Dorfman, David M. et al., "T-bet, a T-Cell-Associated Transcription Factor is Expressed in a Subset of B-Cell Lymphoproliferative Disorders," *Am. J. Clin. Pathol.*, vol. 122:292-297 (2004).

Dorfman, David M. et al., "T-bet, a T-Cell-Associated Transcription Factor is Expressed in Hodgkin's lymphoma," *Human Pathology*, vol. 36:10-15 (2005).
Finotto, Susetta et al., "Asthmatic changes in mice lacking T-bet are mediated by IL-13," *International Immunology*, vol. 17(8):993-1007 (2005).
Finotto, Susetta et al., "Development of Spontaneous Airway Changes Consistent with Human Asthma in Mice Lacking T-bet," *Science*, vol. 295:336-338 (2002).
Garrett. Wendy S. et al., "Communicable Ulcerative Colitis Induced by T-bet Deficiency in the Innate Immune System," *Cell*, vol. 131:33-45 (2007).
Gerth, Andrea J. et al., "An Innate Cell-Mediated, Murine Ulcerative Colitis-like Syndrome in the Absence of Nuclear Factor of Activated T Cells," Gastroenterology, vol. 126:1115-1121 (2004).
Glimcher, Laurie H. et al., "Recent Developments in the Transcriptional Regulation of Cytolytic Effector Cells," Nature, vol. 4:900-911 (2004).
Glimcher, Laurie H., "Trawling for treasure: tales of T-bet," Nature Immunology, vol. 8(5):448-450 (2007).
Ho, I-Cheng et al., "Transcription: Tantalizing Times for T Cells," Cell, vol. 109:S109-S120 (2002).
Hwang, Eun Sook et al., "IL-2 production in developing Th1 cells is regulated by heterodimerization of RelA and T-bet and requires T-bet serine residue 508," J. Exp. Med., vol. 202(9):1289-1300 (2005).
Hwang, Eun Sook et al., "T Helper Cell Fate Specified by Kinase-Mediated Interaction of T-bet with GATA-3," Science, vol. 307:430-433 (2005).
Juedes, Amy E. et al., "T-bet Controls Autoaggressive CD8 Lymphocyte Responses in Type 1 Diabetes," J. Exp. Med., vol. 199(8):1153-1162 (2004).
Lametschwandtner, Günther et al., "Sustained T-bet expression confers polarized human TH2 cells with TH1-like cytokine production and migratory capacities," J. Allergy Clin. Immunol., vol. 113:987-994 (2004).
Lugo-Villarino, Geanncarlo et al., "T-bet is required for optimal production of IFN-γ and antigen-specific T cell activation by dendritic cells," PNAS, vol. 100(13):7749-7754 (2003).
Lugo-Villarino, Geanncarlo et al., "The adjuvant activity of CpG DNA requires T-bet expression in dendritic cells," PNAS, vol. 102(37):13248-13253 (2005).
Lord, Graham M. et al., "T-bet is required for optimal proinflammatory CD4+ T-cell trafficking," Blood, vol. 106(10):3432-3439 (2005).

(Continued)

*Primary Examiner*—Robert Landsman
(74) *Attorney, Agent, or Firm*—Giulio A. DeConti, Jr.; Megan E. Williams; Lahive & Cockfield, LLP

(57) ABSTRACT

The instant invention is based, at least in part, on the dentification of a mechanism by which T-bet modulates IL2 production. The present invention pertains to methods of identifying agents that modulate the kinase-mediated interaction of T-bet with RelA, as well as methods of use therefore.

11 Claims, No Drawings

OTHER PUBLICATIONS

Melanitou, Evie et al., "Absence of the T-bet Gene Coding for the Th1-Related Transcription Factor Does Not Affect Diabetes-Associated Phenotypes in Balb/c Mice," Ann. N.Y. Acad. Sci., vol. 1005:187-191 (2003).

Mowen, Kerri A. et al., "Signaling pathways in Th2 development," Immunological Reviews, vol. 202:203-222 (2004).

Neurath, M.E. et al., "The Transcription Factor T-bet Regulates Mucosal T Cell Activation in Experimental Colitis and Crohn's Disease," J. Exp. Med., vol. 195(9):1129-1143 (2002).

Peng, Stanford L. et al., "T-bet regulates IgG class switching and pathogenic autoantibody production," PNAS, vol. 99(8):5545-5550 (2002).

Peng, Stanford L. et al., "T-bet Regulates Metastasis Rates in a Murine Model of Primary Prostate Cancer," Cancer Research, vol. 64:452-455 (2004).

Raby, Benjamin A. et al., "T-Bet Polymorphisms Are Associated with Asthma and Airway Hyperresponsiveness," Am. J. Respir. Crit. Care Med., vol. 173:64-70 (2006).

Ravindran, Rejesh et al., "Expression of T-bet by CD4 T Cells Is Essential for Resistance to Salmonella Infection," The Journal of Immunology, vol. 174:4603-4610 (2005).

Rosas, Lucia E. et al., "Cutting Edge: STAT1 and T-bet Play Distinct Roles in Determining Outcome of Visceral Leishmaniasis Caused by *Leishmania donovani*," The Journal of Immunology, vol. 177:22-25 (2006).

Shinohara, Mari L. et al., "T-bet-independent expression of osteopontin contributes to T cell polarization," PNAS, vol. 102(47):17101-17106 (2005).

Sullivan, Brandon M. et al., "Antigen-driven effector CD8 T cell function regulated by T-bet," PNAS, vol. 100(26):15818-15823 (2003).

Sullivan, Brandon M. et al., "Increased Susceptibility of Mice Lacking T-bet to Infection with *Mycobacterium tuberculosis* Correlates with Increased IL-10 and Decreased INF-$\gamma$ Production," The Journal of Immunology, vol. 175:4593-4602 (2005).

Szabo, Susanne J. et al., "A Novel Transcription Factor, T-bet, Directs Th1 Lineage Commitment," Cell, vol. 100:655-669 (2000).

Szabo, Susanne J. et al., "Distinct Effects of T-bet in TH1 Lineage Commitment and IFN-$\gamma$ Production in CD4 and CD8 T Cells," Science, vol. 295:338-342 (2002).

Szabo, Susanne J. et al,. "Molecular mechanisms regulating Th1 immune responses," Annu. Rev. Immunol., vol. 21:713-758 (2001).

Tantisira, Kelan G. et al., "TBX21: A functional variant predicts improvement in asthma with the use of inhaled corticosteroids," PNAS, vol. 101(52):18099-18104 (2004).

Taqueti, Viviany R. et al., "T-bet Controls Pathogenicity of CTLs in the Heart by Separable Effects on Migration and Effector Activity," The Journal of Immunology, vol. 177:5890-5901 (2006).

Townsend, Michael J. et al., "T-bet Regulates the Terminal Maturation and Homeostasis of NK and V$\alpha$ 14i NKT Cells," Immunity, vol. 20:477-494 (2004).

Wang, Jinsong et al., "Transcription factor T-bet regulates inflammatory arthritis through its function in dendritic cells," The Journal of Clinical Investigation, vol. 116(2):414-421 (2006).

Yin, Zhinan et al., "T-Bet Expression and Failure of GATA-3 Cross-Regulation Lead to Default Production of IFN-$\gamma$ by $\gamma\delta$ T Cells," The Journal of Immunology, vol. 168:1566-1571 (2002).

International Search Report for Application No. PCT/US06/43429, dated Oct. 10, 2007.

Li, B. et al., "T-bet expression is upregulated in active Behçet's disease," Br. J. Ophthalmol., vol. 87:1264-1267 (2003).

Kashiwakura, Jun-ichi et al., "Txk, a Nonreceptor Tyrosine Kinase of the Tec Family, Is Expressed in T Helper Type 1 Cells and Regulates Interferon $\gamma$ Production in Human T Lymphocytes," J. Exp. Med., vol. 190(8):1147-1154 (1999).

Owaki, Toshiyuki et al., "IL-27 Induces Th1 Differentiation via p38 MAPK/T-bet- and Intercelluar Adhesion Molecule-1/LFA-1/ERK1/2-Dependent Pathways," The Journal of Immunology, vol. 177:7579-7587 (2006).

Schaeffer, Edward M. et al., "Requirement for Tec Kinases Rlk and Itk in T Cell Receptor Signaling and Immunity," Science, vol. 284:638-641 (1999).

Yang, Wen-Chin et al., "Tec kinase is involved in transcriptional regulation of IL-2 and IL-4 in the CD28 pathway," Eur. J. Immunol., vol. 29:1842-1849 (1999).

European Office Action for Application No. 02804492.3, dated Oct. 24, 2008.

MODULATION OF IL-2 PRODUCTION BY T-BET

RELATED APPLICATIONS

This application claims the benefit of U.S. Provisional Application No. 60/734,324, filed Nov. 7, 2005, titled "Modulation of IL-2 Production by T-bet". The entire contents of this application is incorporated herein by this reference.

GOVERNMENT FUNDING

Work described herein was supported, at least in part, under grants CA48126 and AI56296 awarded by the National Institutes of Health. The U.S. government therefore may have certain rights in this invention.

BACKGROUND OF THE INVENTION

The T cell growth factor IL-2 is the major cytokine produced during the primary response of T helper (Th) cells. Upon differentiation into one of the two types of Th effector cells, Th1 and Th2, IL-2 production declines and is replaced by production of Th1-like (IFNγ) or Th2-like (IL-4) cytokines. IL-2 acts through its receptor (IL-2R) to activate signaling molecules involved in cell proliferation; defects in either the ligand or the receptor result in autoimmunity (Schimpl, A., I., et al. 2002. *Cytokine Growth Factor Rev* 13:369-378). Although IL-2 has been previously characterized as a Th1-like cytokine, increasing evidence indicates that IL-2 and its downstream signaling molecule Stat5 are also vital for the induction of anti-inflammatory Th2 cytokines during a primary response (Zhu, J., J., et al. 2003. *Immunity* 19:739-748).

IL-2 expression is tightly controlled at the transcriptional level although posttranscriptional control through coding sequences also occurs (Ragheb, J. A., et al. 1999. *J Immunol* 163:120-129). Extensive analysis of the IL-2 gene has established a minimal promoter region extending -300 bp relative to the transcription start site, known to be sufficient for IL-2 induction upon T cell activation in vitro (Durand, D., et al. 1988. *Mol. Cell. Biol.* 8:1715-1724; Siebenlist, U., et al. 1986. *Mol. Cell. Biol.* 6:3042-3049) (and reviewed in Jain, J., C et al. 1995. *Curr Opin Immunol* 7:333-342; Serfling, E., et al. 1995. *Biochim Biophys Acta* 1263:181-200; Powell, J. D., et al. 1998. *Immunol Rev* 165:287-300; Novak, T. J., P et al. 1990. *Nucleic Acids Res* 18:4523-4533). Multiple cis regulatory elements within this region have been identified that bind antigen-inducible factors such as NFATs, OCT-1, AP-1, HMG I(Y) and NF-κB family members p65 and c-Rel. These factors have been shown to transactivate an IL-2 promoter in transient reporter assays (reviewed in Jain, J., C et al. 1995. *Curr Opin Immunol* 7:333-342; Serfling, E., et al. 1995. *Biochim Biophys Acta* 1263:181-200; Powell, J. D., et al. 1998. *Immunol Rev* 165:287-300; Novak, T. J., P et al. 1990. *Nucleic Acids Res* 18:4523-4533) and some of them are required for IL-2 expression in vivo (Peng, S. L., et al. 2001. *Immunity* 14:13-20; Kontgen, F., et al. 1995. *Genes Dev.* 9:1965-1977; Liou, H. C., et al. 1999. *Int. Immunol.* 11:361-371). NF-κB family members regulate the transcription of the IL-2 gene (Jain, J., C et al. 1995. *Curr Opin Immunol* 7:333-342; Serfling, E., et al. 1995. *Biochim Biophys Acta* 1263:181-200; Powell, J. D., et al. 1998. *Immunol Rev* 165:287-300; Novak, T. J., P et al. 1990. *Nucleic Acids Res* 18:4523-4533). While p50/p50 homodimers are present in large amounts in unstimulated cells, they are inhibitory and are replaced by p50/p65 or p50/c-rel heterodimers upon T cell activation. c-Rel nucleates chromatin remodeling across the IL-2 promoter (Grundstrom, S., et al. 2004. *J Biol Chem* 279:8460-8468; Lai, J. H., et al. 1995. *Mol Cell Biol* 15:4260-4271; Neumann, M., et al. 1995. *Embo J* 14:1991-2004; Ghosh, P., et al. 1993. *Proc Natl Acad Sci USA* 90:1696-1700; Parra, E., et al. 1998. *J Immunol* 160:5374-5381; Herndon, T. M., et al. 2002. *Clin Immunol* 103:145-153; Rao, S., et al. 2003. *J Immunol* 170:3724-3731; Kahn-Perles, B., et al. 1997. *J Biol Chem* 272:21774-21783). Interestingly, increased amounts of the NF-κB p65 (RelA) factor in the nucleus of Th1 than Th2 cells has been reported, consistent with the preferential secretion of IL-2 by Th1 cells (Lederer, J. A., et al. 1994. *J Immunol.* 152:77-86; Dorado, B., et al. 1998. *Eur J Immunol* 28:2234-2244).

Lines of transgenic mice revealed a requirement for additional IL-2 upstream sequence to achieve expression in vivo that faithfully mirrors endogenous IL-2 expression (Yui, M. A., et al. 2001. *J Immunol* 166:1730-1739). The contribution of regions beyond the minimal promoter is also evident from studies that show that selective demethylation of a 600 bp region of an IL-2 enhancer occurs rapidly upon T cell activation (Bruniquel, D., and R. H. Schwartz. 2003. *Nat Immunol* 4:235-240). The function of individual factors that bind IL-2 promoter DNA and the initiation of chromatin remodeling of the IL-2 gene in response to T cell activation has been the subject of several reports (Ward, S. B., et al. 1998. *Nucleic Acids Res* 26:2923-2934; Rothenberg, E. V., and S. B. Ward. 1996. *Proc. Natl. Acad. Sci. USA* 93:9358-9365; Attema, J. L., et al. 2002. *J Immunol* 169:2466-2476; Chen, X., et al. 2005. *Mol Cell Biol* 25:3209-3219; Rao, S., et al. 2001. *J Immunol* 167:4494-4503). The NF-κB subunit c-Rel is required for chromatin remodeling across the proximal promoter and c-Rel binds with HMG I(Y) to the CD28 response element (Rao, S., et al. 2003. *J Immunol* 170:3724-3731; Himes, S. R., et al. 1996. *Immunity* 5:479-489). Mice lacking c-Rel exhibit impaired IL-2 expression, and treatment with the c-Rel inhibitor pentoxifylline reduces IL-2 mRNA levels (Kontgen, F., et al. 1995. *Genes Dev.* 9:1965-1977; Liou, H. C., et al. 1999. *Int. Immunol.* 11:361-371; Wang, W. W., et al. 1997. *Immunity* 6:165-174).

Negative regulation of IL-2 gene transcription is also an important mechanism for controlling its expression. During primary Th1 cell differentiation, IL-2 is rapidly induced and peaks between day 2 and day 3 post TCR stimulation, then gradually decreases. Homodimers of the NF-κB member p50 are thought to repress IL-2 gene transcription in resting Th cells (Grundstrom, S., et al. 2004. *J Biol Chem* 279:8460-8468; Sundstedt, A., et al. 1996. *Proc Natl Acad Sci USA* 93:979-984) and expression of a dominant negative CREB transgene resulted in impaired IL-2 production in vivo (Barton, K., et al. 1996. *Nature* 379:81-85). The CREM transcriptional repressor is activated by CaMKIV to bind to a CRE at position-180 to suppress IL-2 production in patients with SLE (Juang, Y. T., et al. 2005. *J Clin Invest* 115:996-1005; Tenbrock, K., et al. 2002. *J Immunol* 169:4147-4152), and CREM is also involved in establishing the anergic state (Powell, J. D., et al. 1999. *J Immunol* 163:6631-6639). A zinc finger protein named ZEB is thought to be a transcriptional repressor of the IL-2 gene, but its function in primary Th cells has not been established (Yasui, D. H., et al. 1998. *J. Immunol.* 160:4433-4440). The antiproliferative factor Tob represses IL-2 through enhancing Smad binding to the -105 negative regulatory element of the IL-2 promoter (Tzachanis, D., et al. 2001. *Nat Immunol* 2:1174-1182).

The T-box transcription factor, T-bet, has three separable functions: 1) it is required for Th1 development from the Thp, 2) it represses Thp differentiation along the Th2 pathway by inhibiting GATA-3 activity through the physical interaction of tyrosine phosphorylated T-bet and GATA-3, and 3) it represses IL-2 gene activation (Szabo, S. J., et al. 2000. *Cell* 100:655-669; Szabo, S. J., et al. 2002. *Science* 295:338-342; Szabo, S. J., et al. 2003. *Ann. Rev. Immunol.* 21:713-758; Hwang, E. S., S et al. 2005. *Science* 307:430-433). Consequently, T-bet$^{-/-}$ mice exhibit impaired Th1 cell development, increased Th2 cytokine production, and interestingly, increased IL-2 production in both CD4 and CD8 cells (Szabo, S. J., et al. 2002. *Science* 295:338-342; Sullivan, B. M., et al. 2003. *Proc Natl Acad Sci USA* 100:15818-15823; Juedes, A., et al. 2004. *J. Exp. Med.* 199:1153-1162). Indeed, T-bet was originally isolated in a yeast one hybrid screen that utilized the 400 bp IL-2 promoter as substrate and was subsequently shown to repress IL-2 promoter activation (Szabo, S. J., et al. 2000. *Cell* 100:655-669). Further, overexpression of T-bet in T-bet$^{-/-}$ Th cells repressed IL-2 production (Szabo, S. J., et al. 2000. *Cell* 100:655-669; Hwang, E. S., S et al. 2005. *Science* 307:430-433). While the first two functions of T-bet are understood at a molecular level, the mechanism by which T-bet controls production of IL-2 has not been apparent. The identification of the mechanism by which T-bet controls production of IL-2 would be of great benefit.

SUMMARY OF THE INVENTION

The instant invention is based, at least in part, on the identification of the mechanism by which T-bet represses IL2 production. T-bet acts as a repressor of IL-2 gene transcription in developing Th1 cells by an interaction with the RelA NF-κB transcription factor that requires T-bet$^{S508}$ and is associated with T-bet$^{S508}$ phosphorylation. RelA/T-bet heterodimers regulate the binding of RelA to IL-2 promoter DNA and hence its transactivation of IL-2 gene expression.

One aspect of the invention features a method for identifying a compound which modulates interleukin 2 (IL-2) production, comprising contacting in the presence of the compound, T-bet and a serine-threonine kinase molecule under conditions which allow interaction of the kinase molecule with T-bet, and detecting the interaction of T-bet and the kinase molecule, wherein the ability of the compound to increase IL-2 production is indicated by a decrease in the interaction as compared to the amount of interaction in the absence of the compound, and the ability of the compound to decrease IL-2 production is indicated by a increase in the interaction as compared to the amount of interaction in the absence of the compound.

In one embodiment, the interaction of T-bet and the kinase molecule is determined by measuring the formation of a complex between T-bet and the kinase. In another embodiment, the interaction of T-bet and the kinase molecule is determined by measuring the phosphorylation of T-bet. In one embodiment, the phosphorylation of T-bet is determined by measuring the phosphorylation of the serine residue at amino acid position 508 (S508) of T-bet. In one embodiment, the kinase molecule is casein kinase I (CK1). In another embodiment, the kinase molecule is glycogen synthase kinase-3 (GSK-3). In one embodiment, the the production of IL-2 is measured by determining IL-2 mRNA levels. In another embodiment, the production of IL-2 is measured by determining IL-2 protein levels.

Another aspect of the invention features a method of identifying compounds useful in modulating IL-2 production comprising, a) providing an indicator composition comprising T-bet, RelA, and an IL-2 regulatory region; b) contacting the indicator composition with each member of a library of test compounds; c) selecting from the library of test compounds a compound of interest that decreases the T-bet-mediated interaction of RelA and the IL-2 regulatory region to thereby identify a compound that modulates IL-2 production, wherein the ability of the compound to increase IL-2 production is indicated by a decrease in the interaction as compared to the amount of interaction in the absence of the compound, and the ability of the compound to decrease IL-2 production is indicated by a increase in the interaction as compared to the amount of interaction in the absence of the compound.

In one embodiment, the T-bet-mediated interaction of RelA and IL-2 is determined by measuring the formation of a complex RelA and the IL-2 regulatory region. In one embodiment, the indicator composition is a cell that expresses a T-bet polypeptide. In one embodiment, and the IL-2 regulatory region comprises a T-box binding site.

Another aspect of the invention features a method for identifying a compound which modulates the interaction of RelA and an IL-2 regulatory region in a T cell, comprising contacting in the presence of the compound and T-bet, RelA and the IL-2 regulatory region under conditions which allow T-bet-mediated binding of RelA to the IL-2 regulatory region to form a complex; and detecting the formation of a complex of RelA and the IL-2 regulatory region in which the ability of the compound to inhibit interaction between RelA and the IL-2 regulatory region in the presence of T-bet and the compound is indicated by a decrease in complex formation as compared to the amount of complex formed in the absence of T-bet and the compound.

In one embodiment, the compound increases the formation or stability of the complex. In another embodiment, the compound decreases the formation or stability of the complex.

In one embodiment, the agent increases serine phosphorylation of T-bet.

DETAILED DESCRIPTION OF THE INVENTION

The instant invention is based, at least in part, on the identification of a mechanism by which T-bet modulates IL2 production. This invention pertains to, inter alia, methods of identifying agents that modulate the kinase-mediated interaction of T-bet with RelA, as well as methods of use therefore (see appended examples). As discussed in more detail below, T-bet is an important intracellular transducer or mediator of a variety of extracellular signals. More specifically, T-bet is a transcription factor that operates in different cell types to transduce extracellular signals into specific patterns of gene expression. In particular, it has now been demonstrated that T-bet has a central role in both Th1 and Th2 cytokine gene expression. Different cell types and different genes respond to T-bet, which serves to modulate a variety of cellular responses. T-bet also controls expression of several genes, expression of these genes and others similarly affected can be modulated (e.g., enhanced or reduced) by controlling the expression and/or activity of T-bet.

Brachyury or T is the founding member of a family of transcription factors that share a 200 amino acid DNA-binding domain called the T-box (reviewed in Smith, 1997; Papaioannou, 1997; Meisler, 1997). The Brachyury (Greek for 'short tail') mutation was first described in 1927 in heterozygous mutant animals who had a short, slightly kinked tail (Herrmann et al., 1990). The amino-terminal half (amino acids 1-229) of the Brachyury T-box protein contains a conserved domain known as the T box which has been shown to exhibit sequence-specific DNA-binding activity (Kispert, A. & Herrmann, B. G. 1993. *EMBO J.* 12:3211; Papapetrou, C., et al. 1997. *FEBS Lett.* 409:201; Kispert, A., et al. 1995. *EMBO J.* 14:4763). The C-terminal half contains two pairs of transactivation and repression domains. The similarity of sequence between the T box region in orthologous species can be as high as 99% and is around 40-70% between non-orthologous genes. The T-box domain has recently been co-crystallized with DNA and demonstrates a novel sequence-specific DNA recognition architecture in which the protein contacts DNA in both the major and minor grooves (Müller, C. W. & Herrmann, B. G. 1997. *Nature* 389, 884).

A yeast one hybrid approach was used to identify Th-1 specific transcription factors. Yeast cells were made to express an IL-2 promoter-reporter gene construct and were transformed with a cDNA library made from an anti-CD3 activated Th1 cell clone. Inspection of the IL-2 promoter reveals an excellent T-box binding site at -240 to -220 just 5' of the NFkB site. As described in the appended examples, T-bet was isolated in a yeast one hybrid screening assay based on its ability to bind to the IL-2 promoter.

The T-bet proteins of the invention have homology to T-box proteins. There are now more than eight T-box genes in the mouse not including Brachyury. These include Tbx 1-6, T-brain-1 (Thr-1), Eomes, T-pit, and T-bet, each with a distinct and usually complex expression pattern. T-brain-1 expression, for example is largely restricted to distinct domains within the cerebral cortex (Bulfone, A., et al. 1995. *Neuron* 15, 63). T-bet is most similar in sequence to Tbr-1. Outside of the T-box, the T-bet proteins of the invention bear no similarity to other T-box proteins.

T-bet is most similar in sequence to Tbr-1. Other species also express Brachyury-like genes. Such vertebrate species include *Xenopus*, zebrafish, chick and humans (Rao, 1994; Horb and Thomsen, 1997; Conlon et al., 1996; Ryan et al., 1996; Schulte-Merker et al., 1994; Edwards et al., 1996; Morrison et al., 1996; Law et al., 1995; Campbell et al., 1998) as well as more distant species such as amphioxus, ascidians, echinoderms, *Caenorhabditis elegans, Drosophila* and other insects (Holland et al., 1995). These genes are conserved both in sequence and in expression pattern.

So that the invention may be more readily understood, certain terms are first defined.

As used herein, the term "modulated" with respect to T-bet includes changing the expression, activity or function of T-bet in such a manner that it differs from the naturally-occurring expression, function or activity of T-bet under the same conditions. For example, the expression, function or activity can be greater or less than that of naturally occurring T-bet, e.g., owing to a change in binding specificity, etc. As used herein, the various forms of the term "modulate" include stimulation (e.g., increasing or upregulating a particular response or activity) and inhibition (e.g., decreasing or downregulating a particular response or activity).

As used herein, the term "T-bet molecules" includes T-bet nucleic acid molecules that share structural features with the nucleic acid molecules shown in SEQ ID NOs: 1 and 3 and T-bet proteins that share the distinguishing structural and functional features of the T-bet proteins shown in SEQ ID Nos: 2 and 4. The T-bet proteins are members of the T-box family of proteins and share some amino acid sequence homology to Brachyury, Tbx1-6, T-brain-1 (Tbr-1). T-box proteins comprise a T-box domain which binds to DNA at a T-box binding site. Further structural and functional features of T-bet proteins are provided below.

As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA. The term "equivalent" is intended to include nucleotide sequences encoding function-ally equivalent T-bet proteins, i.e., proteins which have the ability to interact, e.g., bind, to the natural binding partners of T-bet.

An used herein, an "isolated nucleic acid molecule" refers to a nucleic acid molecule that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). For example, in various embodiments, an isolated T-bet nucleic acid molecule typically contains less than about 10 kb of nucleotide sequences which naturally flank the nucleic acid molecule in genomic DNA of the cell from which the nucleic acid is derived, and more preferably contains less than about 5 kb, 4 kb, 3 kb, 2 kb, 1 kb, 0.5 kb or 0.1 kb of naturally flanking nucleotide sequences. An "isolated" T-bet nucleic acid molecule may, however, be linked to other nucleotide sequences that do not normally flank the T-bet sequences in genomic DNA (e.g., the T-bet nucleotide sequences may be linked to vector sequences). In certain preferred embodiments, an "isolated" nucleic acid molecule, such as a cDNA molecule, also may be free of other cellular material. However, it is not necessary for the T-bet nucleic acid molecule to be free of other cellular material to be considered "isolated" (e.g., a T-bet DNA molecule separated from other mammalian DNA and inserted into a bacterial cell would still be considered to be "isolated").

The nucleic acids of the invention can be prepared, e.g., by standard recombinant DNA techniques. A nucleic acid of the invention can also be chemically synthesized using standard techniques. Various methods of chemically synthesizing polydeoxynucleotides are known, including solid-phase synthesis which has been automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

As used herein, the term "hybridizes under high stringency conditions" is intended to describe conditions for hybridization and washing under which nucleotide sequences having substantial homology (e.g., typically greater than 70% homology) to each other remain stably hybridized to each other. A preferred, non-limiting example of high stringency conditions are hybridization in a hybridization buffer that contains 6× sodium chloride/sodium citrate (SSC) at a temperature of about 45° C. for several hours to overnight, followed by one or more washes in a washing buffer containing 0.2×SSC, 0.1% SDS at a temperature of about 50-65° C.

The term "percent (%) identity" as used in the context of nucleotide and amino acid sequences (e.g., when one amino acid sequence is said to be X % identical to another amino acid sequence) refers to the percentage of identical residues shared between the two sequences, when optimally aligned. To determine the percent identity of two nucleotide or amino acid sequences, the sequences are aligned for optimal comparison purposes (e.g., gaps may be introduced in one sequence for optimal alignment with the other sequence). The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions×100).

Computer algorithms known in the art can be used to optimally align and compare two nucleotide or amino acid sequences to define the percent identity between the two sequences. A preferred, non-limiting example of a mathematical algorithm utilized for the comparison of two sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the NBLAST and XBLAST programs of Altschul, et al. ((1990) J. Mol. Biol. 215:403-10). To obtain gapped alignments for comparison purposes, Gapped BLAST can be utilized as described in Altschul et al. ((1997) Nucleic Acids Research 25(17):3389-3402).When utilizing BLAST and Gapped BLAST programs, the default parameters of the respective programs (e.g., XBLAST and NBLAST) can be used. For example, the nucleotide sequences of the invention were blasted using the default Blastn matrix 1-3 with gap penalties set at: existence 5 and extension 2. The amino acid sequences of the invention were blasted using the default settings: the Blosum62 matrix with gap penalties set at existance 11 and extension 1.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. If multiple programs are used to compare sequences, the program that provides optimal alignment (i e., the highest percent identity between the two sequences) is used for comparison purposes.

As used herein, a "naturally-occurring" nucleic acid molecule refers to an RNA or DNA molecule having a nucleotide sequence that occurs in nature (e.g., encodes a natural protein).

As used herein, the term "promoter", "regulatory region", or "promotor element" means a nucleic acid sequence which is required for expression of a gene product operably linked to the promoter/regulatory sequence. In some instances, this sequence may be the core promoter sequence and in other instances, this sequence may also include enhancer sequences and other regulatory elements, such as for example a T-box binding site, which are required for expression of the gene product. The promoter/regulatory sequence may, for example, be one which expresses the gene product in a spatially or temporally restricted manner.

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, nucleic acid molecule of the invention is an siRNA molecule. In one embodiment, a nucleic acid molecule of the invention mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999); Cottrell T R, and Doering T L. 2003. Trends Microbiol. 11:37-43; Bushman F. 2003. Mol Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described above for use in antisense RNA can be employed in molecules that mediate RNAi.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions). These noncoding regions may contain various regulatory elements.

As used herein, the term "promoter", "regulatory region", "promotor element", or "regulatory elements" means a nucleic acid sequence which is required for expression of a gene product operably linked to the promoter/regulatory sequence. In some instances, this sequence may be the core promoter sequence and in other instances, this sequence may also include enhancer sequences and other regulatory elements, such as for example a T-box binding site, which are required for expression of the gene product. The promoter/regulatory sequence may, for example, be one which expresses the gene product in a spatially or temporally restricted manner.

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" or "isolated polypeptide" refers to a protein or polypeptide that is substantially free of other proteins, polypeptides, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the protein is derived, or substantially free from chemical precursors or other chemicals when chemically synthesized. The language "substantially free of cellular material" includes preparations of T-bet protein in which the protein is separated from cellular components of the cells from which it is isolated or recombinantly produced.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and $F(ab')_2$ fragments. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody compositions thus typically display a single binding affinity for a particular antigen with which it immunoreacts.

As used here, the term "intrabodies" refers to intracellularly expressed antibody constructs, usually single-chain Fv (scFv) antibodies, directed against a target inside a cell, e.g. an intracellular protein such as T-bet.

As used herein, the term "dominant negative T-bet protein" includes T-bet molecules (e.g., portions or variants thereof) that compete with native (i.e., naturally occurring wild-type) T-bet molecules, but which do not have T-bet activity. Such molecules effectively decrease T-bet activity in a cell. As used herein, "dominant negative T-bet protein" refers to a modified form of T-bet which is a potent inhibitor of T-bet activity.

As used herein, the term "cell" includes prokaryotic and eukaryotic cells. In one embodiment, a cell of the invention is a bacterial cell. In another embodiment, a cell of the invention is a fungal cell, such as a yeast cell. In another embodiment, a cell of the invention is a vertebrate cell, e.g., an avian or mammalian cell. In a preferred embodiment, a cell of the invention is a murine or human cell.

As used herein, the term "immune cell" includes cells that are of hematopoietic origin and that play a role in the immune response. Immune cells include lymphocytes, such as B cells and T cells; natural killer cells; and myeloid cells, such as monocytes, macrophages, eosinophils, mast cells, basophils, and granulocytes.

The terms "antigen presenting cell" and "APC", as used interchangeably herein, include professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

As used herein, the term "T cell" (i.e., T lymphocyte) is intended to include all cells within the T cell lineage, including thymocytes, immature T cells, mature T cells and the like, from a mammal (e.g., human). T cells include mature T cells that express either CD4 or CD8, but not both, and a T cell receptor. The various T cell populations described herein can be defined based on their cytokine profiles and their function.

As used herein "progenitor T cells" ("Thp") are naive, pluripotent cells that express CD4.

As used herein, the term "naïve T cells" includes T cells that have not been exposed to cognate antigen and so are not activated or memory cells. Naïve T cells are not cycling and human naive T cells are CD45RA+. If naïve T cells recognize antigen and receive additional signals depending upon but not limited to the amount of antigen, route of administration and timing of administration, they may proliferate and differentiate into various subsets of T cells, e.g., effector T cells.

As used herein, the term "peripheral T cells" refers to mature, single positive T cells that leave the thymus and enter the peripheral circulation.

As used herein, the term "differentiated" refers to T cells that have been contacted with a stimulating agent and includes effector T cells (e.g., Th1, Th2) and memory T cells. Differentiated T cells differ in expression of several surface proteins compared to naïve T cells and secrete cytokines that activate other cells.

As used herein, the term "memory T cell" includes lymphocytes which, after exposure to antigen, become functionally quiescent and which are capable of surviving for long periods in the absence of antigen. Human memory T cells are CD45RA-.

As used herein, the term "effector T cell" includes T cells which function to eliminate antigen (e.g., by producing cytokines which modulate the activation of other cells or by cytotoxic activity). The term "effector T cell" includes T helper cells (e.g., Th1 and Th2 cells) and cytotoxic T cells. Th1 cells mediate delayed type hypersensitivity responses and macrophage activation while Th2 cells provide help to B cells and are critical in the allergic response (Mosmann and Coffman, 1989, *Annu. Rev. Immunol.* 7, 145-173; Paul and Seder, 1994, *Cell* 76, 241-251; Arthur and Mason, 1986, *J. Exp. Med.* 163, 774-786; Paliard et al., 1988, *J. Immunol.* 141, 849-855; Finkelman et al., 1988, *J. Immunol.* 141, 2335-2341). As used herein, the term "T helper type 1 response" (Th1 response) refers to a response that is characterized by the production of one or more cytokines selected from IFN-γ, IL-2, TNF, and lymphotoxin (LT) and other cytokines produced preferentially or exclusively by Th1 cells rather than by Th2 cells.

As used herein, the term "regulatory T cell" includes T cells which produce low levels of IL-2, IL-4, IL-5, and IL-12. Regulatory T cells produce TNFα, TGFβ, IFN-γ, and IL-10, albeit at lower levels than effector T cells. Although TGFβ is the predominant cytokine produced by regulatory T cells, the cytokine is produced at lower levels than in Th1 or Th2 cells, e.g., an order of magnitude less than in Th1 or Th2 cells. Regulatory T cells can be found in the CD4+CD25+ population of cells (see, e.g., Waldmann and Cobbold. 2001. *Immunity.* 14:399). Regulatory T cells actively suppress the proliferation and cytokine production of Th1, Th2, or naïve T cells which have been stimulated in culture with an activating signal (e.g., antigen and antigen presenting cells or with a signal that mimics antigen in the context of MHC, e.g., anti-CD3 antibody plus anti-CD28 antibody).

As used herein, the term "cellular differentiation" includes the process by which the developmental potential of cells is restricted and they acquire specific developmental fates. Differentiated cells are recognizably different from other cell types.

As used herein, the term "receptor" includes immune cell receptors that bind antigen, complexed antigen (e.g., in the context of MHC molecules), or antibodies. Activating receptors include T cell receptors (TCRs), B cell receptors (BCRs), cytokine receptors, LPS receptors, complement receptors, and Fc receptors. For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

As used herein, the term "immune response" includes immune cell-mediated (e.g., T cell and/or B cell-mediated) immune responses that are influenced by modulation of immune cell activation. Exemplary immune responses include B cell responses (e.g., antibody production, e.g., IgA production), T cell responses (e.g., proliferation, cytokine production and cellular cytotoxicity), and activation of cytokine responsive cells, e.g., macrophages. In one embodiment of the invention, an immune response is T cell mediated. In another embodiment of the invention, an immune response is B cell mediated. As used herein, the term "downregulation" with reference to the immune response includes a diminution in any one or more immune responses, preferably T cell responses, while the term "upregulation" with reference to the immune response includes an increase in any one or more immune responses, preferably T cell responses. It will be understood that upregulation of one type of immune response may lead to a corresponding downregulation in another type of immune response. For example, upregulation of the production of certain cytokines (e.g., IL-10) can lead to downregulation of cellular immune responses.

As used herein, the term "T helper type 1 response" refers to a response that is characterized by the production of one or more cytokines selected from IFN-γ, IL-2, TNF, and lymphtoxin (LT) and other cytokines produced preferentially or exclusively by Th1 cells rather than by Th2 cells.

As used herein, a "T helper type 2 response" (Th2 response) refers to a response by CD4+ T cells that is characterized by the production of one or more cytokines selected from IL-4, IL-5, IL-6 and IL-10, and that is associated with efficient B cell "help" provided by the Th2 cells (e.g., enhanced IgG1 and/or IgE production).

As used herein, the term "contacting" (i.e., contacting a cell e.g. a cell, with a compound) includes incubating the compound and the cell together in vitro (e.g., adding the compound to cells in culture) as well as administering the compound to a subject such that the compound and cells of the subject are contacted in vivo. The term "contacting" does not include exposure of cells to an T-bet modulator that may occur naturally in a subject (i.e., exposure that may occur as a result of a natural physiological process).

As described in the appended Examples, T-bet modulates the production of IL2. In one embodiment, the T-bet activity is a direct activity, such as an association with a T-bet-target molecule or complex of T-bet with a binding partner, e.g., RelA or a kinase, e.g., a serine-threonine kinase, e.g., a CKI or GSK-3 kinase. As used herein, the term "target molecule" or "binding partner" is a molecule with which T-bet binds or interacts in nature, and which interaction results in a biological response. The target molecule can be a protein or a nucleic acid molecule. Exemplary target molecules of the invention include proteins in the same signaling pathway as the T-bet protein, e.g., proteins which may function upstream (including both stimulators and inhibitors of activity) or downstream of the T-bet protein in a pathway involving for example, modulation of IL2 production. Exemplary T-bet target molecules include kinases, e.g., serine-threonine kinases, e.g., a CKI or GSK-3 kinase, or DNA sequences with which T-bet interacts to modulate gene transcription.

As used herein, the term "gene whose transcription is regulated by T-bet", includes genes having a regulatory region regulated by T-bet. Such genes can be positively or negatively regulated by T-bet. The term also includes genes which are indirectly modulated by T-bet, i.e., are modulated as the result of the activation of a signaling pathway in which T-bet is involved. Exemplary genes regulated by T-bet include, for example, GATA3, and the cytokine genes, e.g., IL-2, IFN-γ, IL-4, IL-5, TNFα, TGF-β, LT (lymphotoxin), and IL-10.

As used herein, the term "Th1-associated cytokine" is intended to refer to a cytokine that is produced preferentially or exclusively by Th1 cells rather than by Th2 cells. Examples of Th1-associated cytokines include IFN-γ, IL-2, TNF, and lymphtoxin (LT).

As used herein, the term "Th2-associated cytokine" is intended to refer to a cytokine that is produced preferentially or exclusively by Th2 cells rather than by Th1 cells. Examples of Th1-associated cytokines include IL-4, IL-5, and IL-10.

The term "interact" as used herein is meant to include detectable interactions between molecules, such as can be detected using, for example, a yeast two hybrid assay or coimmunoprecipitation. The term interact is also meant to include "binding" interactions between molecules. Interactions may be protein-protein or protein-nucleic acid in nature.

The term "agent" or "compound" or "test compound" includes reagents or test agents which are employed in the methods or assays or present in the compositions of the invention. The term "agent" or "compound" or "test compound" includes compounds that have not previously been identified as, or recognized to be, a modulator of T-bet expression or activity. In one embodiment, more than one compound, e.g., a plurality of compounds, can be tested at the same time in a screening assay for their ability to modulate expression and/or activity of T-bet or a molecule acting upstream or downstream of T-bet in a signal transduction pathway. The term "library of test compounds" refers to a panel comprising a multiplicity of test compounds.

In one embodiment, the term "agent" or "compound" or "test compound" excludes naturally occurring compounds such as cytokines. In another embodiment, the term agent excludes antibodies which bind to naturally occurring cytokines. In another embodiment, the term "agent" excludes antibodies that bind to cytokine receptors. In yet another embodiment, the term "agent" excludes those agents that transduce signals via the T cell receptor, e.g., antigen in the context of an MHC molecule or antibody to a component of the T cell receptor complex. In one embodiment, the agent or test compound is a compound that directly interacts with T-bet or directly interacts with a molecule with which T-bet interacts (e.g., a compound that inhibits or stimulates the interaction between T-bet and a T-bet target molecule, e.g., DNA or another protein). In another embodiment, the compound is one that indirectly modulates T-bet expression and/or activity, e.g., by modulating the activity of a molecule that is upstream or downstream of T-bet in a signal transduction pathway involving T-bet. Such compounds can be identified using screening assays that select for such compounds, as described in detail below.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282: 63), and natural product extract libraries. In another embodiment, the compounds are small, organic non-peptidic compounds. In a further embodiment, a small molecule is not biosynthetic.

As used herein, the term "test compound" includes a compound that has not previously been identified as, or recognized to be, a modulator of T-bet activity and/or expression and/or a modulator of cell growth, survival, differentiation and/or migration.

The term "library of test compounds" is intended to refer to a panel comprising a multiplicity of test compounds.

As used herein, the term "engineered" (as in an engineered cell) refers to a cell into which a nucleic acid molecule encoding the T-bet protein has been introduced.

As used herein, the term "reporter gene" refers to any gene that expresses a detectable gene product, e.g., RNA or protein. Preferred reporter genes are those that are readily detectable. The reporter gene may also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368) and green fluorescent protein (U.S. Pat. No. 5,491,084; WO 96/23898).

As used herein, the term "T-bet-responsive element" refers to a DNA. sequence that is directly or indirectly regulated by the activity of T-bet (whereby activity of T-bet can be monitored, for example, via transcription of the reporter genes).

As used herein, the term "cells deficient in T-bet" is intended to include cells of a subject that are naturally deficient in T-bet, as wells as cells of a non-human T-bet deficient animal, e.g., a mouse, that have been altered such that they are deficient in T-bet. The term "cells deficient in T-bet" is also intended to include cells isolated from a non-human T-bet deficient animal or a subject that are cultured in vitro.

As used herein, the term "cell free composition" refers to an isolated composition which does not contain intact cells. Examples of cell free compositions include cell extracts and compositions containing isolated proteins.

As used herein, the term "indicator composition" refers to a composition that includes a protein of interest (e.g., T-bet), for example, a cell that naturally expresses the protein, a cell that has been engineered to express the protein by introducing an expression vector encoding the protein into the cell, or a cell free composition that contains the protein (e.g., purified naturally-occurring protein or recombinantly-engineered protein).

As used herein, the term "a modulator of T-bet" includes a modulator of T-bet expression, processing, post-translational modification, or activity. The term includes agents, for example a compound or compounds which modulates transcription of a T-bet gene, processing of a T-bet mRNA, translation of T-bet mRNA, post-translational modification of a T-bet protein (e.g., glycosylation, ubiquitinization or phosphorylation) or activity of a T-bet protein. A "modulator of T-bet activity" includes compounds that directly or indirectly modulate T-bet activity. For example, an indirect modulator of T-bet activity may modulate a signal transduction pathway that includes T-bet. Examples of modulators that directly modulate T-bet activity include antisense nucleic acid molecules that bind to T-bet mRNA or genomic DNA, intracellular antibodies that bind to T-bet intracellularly and modulate (i.e., inhibit) T-bet activity, T-bet peptides that inhibit the interaction of T-bet with a target molecule and expression vectors encoding T-bet that allow for increased expression of T-bet activity in a cell, dominant negative forms of T-bet, chemical compounds that act to specifically modulate the activity of T-bet.

As used herein an "agonist" of the T-bet proteins can retain substantially the same, or a subset, of the biological activities of the naturally occurring form of a T-bet protein. An "antagonist" of a T-bet protein can inhibit one or more of the activities of the naturally occurring form of the T-bet protein by, for example, competitively modulating a cellular activity of a T-bet protein.

As used interchangeably herein, "T-bet activity," "biological activity of T-bet" or "functional activity T-bet," include an activity exerted by T-bet protein on a T-bet responsive cell or tissue, e.g., a T cell or on a T-bet target molecule, e.g., a nucleic acid molecule or protein target molecule, as determined in vivo, or in vitro, according to standard techniques. In one embodiment, T-bet activity is a direct activity, such as an association with a T-bet-target molecule. Alternatively, a T-bet activity is an indirect activity, such as a downstream biological event mediated by interaction of the T-bet protein with a T-bet target molecule. Biological activities of T-bet are herein and/or are known in the art. These findings provide for the use of T-bet (and other molecules in the pathways in which T-bet is involved) as drug targets and as targets for therapeutic intervention in various diseases, disorders or conditions. The invention yet further provides immunomodulatory compositions, such as vaccines, comprising agents which modulate T-bet activity.

As used herein, the term "signal transduction pathway" includes the means by which a cell converts an extracellular influence or signal (e.g., a signal transduced by a receptor on the surface of a cell, such as a cytokine receptor or an antigen receptor) into a cellular response (e.g., modulation of gene transcription). Exemplary signal transduction pathways include the JAK1/STAT-1 pathway (Leonard, W. 2001. Int. J. Hematol. 73:271) and the TGF-β pathway (Attisano and Wrana. 2002. Science. 296:1646) A "signal transduction pathway involving T-bet" is one in which T-bet is a signaling molecule which relays signals.

As used herein, a "kinase" is a phosphotransferases or diphosphotransferases molecule of the transferase class [EC 2.7.1-6] that catalyze the transfer of a high-energy phosphate group from a donor compound (e.g., ATP or GTP) to an acceptor compound (alcohol, carboxyl, nitrogenous group, or another phosphate group).

As used herein, a "serine-threonine kinase" is a kinase that catalyzes the phosphorylation of serine or threonine residues in polypeptides, using an ATP molecule or other nucleotides as phosphate donors. Examples of serine-threonine kinases include but are not limited to casein kinase I (CK1) and glycogen synthase kinase-3 (GSK-3).

As used herein, "casein kinase I" or "CKI" is a serine-threonine protein kinase with seven isoforms identified in mammals (α, β, δ, ε, γ1, γ2, and γ3; reviewed in (Gross, S. D. & Anderson, R. A. (1998) Cell. Signal. 10, 699-671 and Knippschild U., et al. (2005) Cell Signal. 17(6):675-89, the contents of each of which are incorporated herein by reference). The kinase domain is highly conserved between members of the CKI family but unique N- and C-terminal tails characterize each isoform. In yeast, the functions of CKI have been much more extensively studied compared to their mammalian counterparts. Extracellular stimuli, the subcellular localization of CK1 isoforms, their interaction with various cellular structures and proteins, as well as autophosphorylation and proteolytic cleavage of their C-terminal regulatory domains influence CK1 kinase activity. Mammalian CK1 isoforms phosphorylate many different substrates among them key regulatory proteins involved in the control of cell differentiation, proliferation, chromosome segregation and circadian rhythms. Deregulation and/or the incidence of mutations in the coding sequence of CK1 isoforms have been linked to neurodegenerative diseases and cancer. The nucleotide and amino acid sequences of human CKI are known and can be found in gi:68303571; gi:20544143; gi:20544144; gi:40549399; gi:40549400; gi:71773653; gi:71773691; gi:21314777; gi:73532777; the contents of all of which are incorporated by reference. The nucleotide and amino acid sequences of mouse CKI are known and can be found in gi:22165381; gi:76496489; gi:31542424; gi:71773562; gi:19527223; gi:22779896; the contents of all of which are incorporated by reference.

As used herein, "glycogen synthase kinase-3" or "GSK-3" is a serine-threonine protein kinase with two isoforms (alpha and beta) identified in mammals (reviewed in Bradley W. Doble and James R. Woodgett (2003) Journal of Cell Science 116, 1175-1186. the contents of which are incorporated by reference). GSK-3 is a multifunctional serine/threonine kinase found in all eukaryotes. The enzyme is a key regulator of numerous signalling pathways, including cellular responses to Wnt, receptor tyrosine kinases and G-protein-coupled receptors and is involved in a wide range of cellular processes, ranging from glycogen metabolism to cell cycle regulation and proliferation. GSK-3 is unusual in that it is normally active in cells and is primarily regulated through inhibition of its activity. Furthermore, compared with other protein kinases is its preference for primed substrates, that is, substrates previously phosphorylated by another kinase. The nucleotide and amino acid sequences of human GSK-3 are known and can be found in gi:49574531; gi:21361339; the contents of all of which are incorporated by reference. The nucleotide and amino acid sequences of mouse GSK-3 are known and can be found in gi:58000432; the contents of which is incorporated by reference.

As used herein, "RelA" is a member of the NF-κB/Rel transcription factor family whose members function as dimers held latently in the the cytoplasm of cells by a family of inhibitor IκB proteins (reviewed in Sha W C. (1998) Exp Med. 19; 187(2):143-6, the contents of which are incorporated herein by reference). There are five known mammalian NF-κB/Rel proteins: Rel (c-Rel), p65 (RelA), RelB, p50 (NFKB1), and p52 (NFKB2). Both the p105 precursor of p50, and the p100 precursor of p52, possess domains that function as IκBs, and there exist at least five distinct IκB proteins: IκBα, IκBβ, IκBε, IκBγ, and bcl-3.

NF-κB/Rel transcription factors are activated by a surprising variety of different signaling pathways involved in immune function and development. Signaling pathways involved in innate immune responses that activate these factors include a newly identified human homologue of *Drosophila* Toll, the cytokines TNF-α and IL-1α, the chemotactic peptide fMet-Leu-Phe, as well a variety of different bacterial and viral products. Signaling pathways involved in adaptive immune responses that activate these factors include key lymphocyte receptor signaling pathways such as antigen receptors on B and T cells, CD28 on T cells, and CD40 on B cells. These signaling pathways converge on phosphorylation and degradation of IκBs, which unmask a nuclear localization signal that leads to translocation of NF-κB/Rel dimers into the nucleus. The nucleotide and amino acid sequences of human RelA are known and can be found in gi:46430498; the contents of which are incorporated by reference. The nucleotide and amino acid sequences of mouse RelA are known and can be found in gi:62899057; the contents of which are incorporated by reference.

As used herein, "interleukin-2" or "IL-2" is a Th1-associated cytokine. IL-2 is a protein of 133 amino acids (15.4 kDa) with a slightly basic pI that is synthesized as a precursor protein of 153 amino acids with the first 20 aminoterminal amino acids functioning as a hydrophobic secretory signal sequence. The protein contains a single disulfide bond (positions Cys58/105) essential for biological activity. IL-2 does not display sequence homology to any other factors, however, murine and human IL-2 display a homology of approximately 65 percent. IL-2 is O-glycosylated at threonine at position 3. Variants with different molecular masses and charges are due to variable glycosylation. Non-glycosylated IL2 is also biologically active. IL-2 has numerous biological functions, such as, for example, Th1 cell proliferation. The nucleotide and amino acid sequences of human IL-2 are known and can be found in gi:28178860; the contents of which are incorporated by reference. The nucleotide and amino acid sequences of mouse IL-2 are known and can be found in gi:31982837; the contents of which are incorporated by reference.

In various embodiments, a regulatory region of the IL-2 gene can be used in the methods of the invention. For example, IL-2 contains numerous regulatory elements and binding sites in the proximal promotor region, such as, for example, NFAT family member binding sites, NF-κB family member binding sites, such as p65 and Rel family members, T-box binding sites, OCT-1 binding sites, AP-1 binding sites, and HMGI(Y) binding sites. Accordingly, the invention further encompasses a regulatory region of IL-2 that includes a T-box binding domain. In various embodiments, this regulatory region encompasses at least nucleotides −254 to −188 relative to the +1 start site of transcription of the interleukin-2 gene of human T-bet.

Various aspects of the invention are described in further detail in the following subsections:

I. Isolated Nucleic Acid Molecules

One aspect of the invention pertains to isolated nucleic acid molecules that encode T-bet. In a preferred embodiment, the nucleic acid molecule of the invention comprises the nucleotide sequence shown in SEQ ID NO:1 or SEQ ID NO:3. In another embodiment, a nucleic acid molecule of the invention comprises at least about 700 contiguous nucleotides of SEQ ID NO:1 or at least about 500 contiguous nucleotides of SEQ ID NO:3. In a preferred embodiment, a nucleic acid molecule of the invention comprises at least about 800, at least about 1000, at east about 1200, at least about 1400 or at least about 1600 contiguous nucleotides of SEQ ID NO:1. In another preferred embodiment, a nucleic acid molecule of the invention comprises at least about 600, at least about 800, at least about 1000, at least about 1200, or at least about 1400 contiguous nucleotides of SEQ ID NO:3.

In other embodiments, the nucleic acid molecule has at least 70% identity, more preferably 80% identity, and even more preferably 90% identity with a nucleic acid molecule comprising: at least about 700, at least about 800, at least about 1000, at east about 1200, at least about 1400 or at least about 1600 contiguous nucleotides of SEQ ID NO:1. In other embodiments, the nucleic acid molecule has at least 70% identity, more preferably 80% identity, and even more preferably 90% nucleotide identity with a nucleic acid molecule comprising: at least about 600, at least about 800, at least about 1000, at least about 1200, or at least about 1400 contiguous nucleotides of SEQ ID NO:3.

Nucleic acid molecules that differ from SEQ ID NO: 1 or 3 due to degeneracy of the genetic code, and thus encode the same T-bet protein as that encoded by SEQ ID NO: 1 and 3, are encompassed by the invention. Accordingly, in another embodiment, an isolated nucleic acid molecule of the invention has a nucleotide sequence encoding a protein having an amino acid sequence shown in SEQ ID NO: 2 or SEQ ID NO:4.

In addition, nucleic acid molecules encoding T-bet proteins can be isolated from other sources using standard molecular biology techniques and the sequence information provided herein. For example, a T-bet DNA can be isolated from a human genomic DNA library using all or portion of SEQ ID NO:1 or 3 as a hybridization probe and standard hybridization techniques (e.g., as described in Sambrook, J., et al. *Molecular Cloning: A Laboratory Manual.* 2nd, ed., Cold Spring Harbor Laboratory, Cold Spring Harbor, N.Y., 1989). Moreover, a nucleic acid molecule encompassing all or a portion of a T-bet gene can be isolated by the polymerase chain reaction using oligonucleotide primers designed based upon the sequence of SEQ ID NO: 1 or 3. For example, mRNA can be isolated from cells (e.g., by the guanidinium-thiocyanate extraction procedure of Chirgwin et al. (1979) *Biochemistry* 18: 5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1 or 3. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a T-bet nucleotide sequence can be prepared by standard synthetic techniques, e.g., using an automated DNA synthesizer.

In addition to the T-bet nucleotide sequence shown in SEQ ID NO: 1 and 3, it will be appreciated by those skilled in the art that DNA sequence polymorphisms that lead to minor changes in the nucleotide or amino acid sequences of T-bet may exist within a population. Such genetic polymorphism in the T-bet gene may exist among individuals within a population due to natural allelic variation. Such natural allelic variations can typically result in 1-2% variance in the nucleotide sequence of the a gene. Any and all such nucleotide variations and resulting amino acid polymorphisms in T-bet that are the result of natural allelic variation and that do not alter the functional activity of T-bet are intended to be within the scope of the invention.

Nucleic acid molecules corresponding to natural allelic variants of the T-bet DNAs of the invention can be isolated based on their homology to the T-bet nucleic acid molecules disclosed herein using the human DNA, or a portion thereof, as a hybridization probe according to standard hybridization techniques under high stringency hybridization conditions. Exemplary high stringency conditions include hybridization in a hybridization buffer that contains 6× sodium chloride/sodium citrate (SSC) at a temperature of about 45° C. for several hours to overnight, followed by one or more washes in a washing buffer containing 0.2×SSC, 0.1% SDS at a temperature of about 50-65° C. Accordingly, in another embodiment, an isolated nucleic acid molecule of the invention hybridizes under high stringency conditions to a second nucleic acid molecule comprising the nucleotide sequence of SEQ ID NO: 1 or 3. Preferably, an isolated nucleic acid molecule of the invention that hybridizes under high stringency conditions to the sequence of SEQ ID NO: of SEQ ID NO:1 or 3. In one embodiment, such a nucleic acid molecule is at least about 700, 800, 900, 1000, 1200, 1300, 1400, 1500, or 1600 nucleotides in length. In another embodiment, such a nucleic acid molecule and comprises at least about 700, 800, 900, 1000, 1200, 1300, 1400, 1500, or 1600 contiguous nucleotides of SEQ ID NO: 1 or at least about 500, 600, 700, 800, 900, 1000, 1100, 1200, 1300, 1400, or 1500 contiguous nucleotides of SEQ ID NO: 3. Preferably, an isolated nucleic acid molecule corresponds to a naturally-occurring allelic variant of a T-bet nucleic acid molecule.

In addition to naturally-occurring allelic variants of the T-bet sequence that may exist in the population, the skilled artisan will further appreciate that minor changes may be introduced by mutation into the nucleotide sequence of SEQ ID NO: 1 or 3, thereby leading to changes in the amino acid sequence of the encoded protein, without altering the functional activity of the T-bet protein. For example, nucleotide substitutions leading to amino acid substitutions at "non-essential" amino acid residues may be made in the sequence of SEQ ID NO: 1 or 3. A "non-essential" amino acid residue is a residue that can be altered from the wild-type sequence of T-bet (e.g., the sequence of SEQ ID NO: 1 or 3) without altering the functional activity of T-bet, such as its ability to interact with DNA or its ability to enhance transcription from an IFN-γ promoter, whereas an "essential" amino acid residue is required for functional activity.

Accordingly, another aspect of the invention pertains to nucleic acid molecules encoding T-bet proteins that contain changes in amino acid residues that are not essential for T-bet activity. Such T-bet proteins differ in amino acid sequence from SEQ ID NO: 2 or 4 yet retain T-bet activity. An isolated nucleic acid molecule encoding a non-natural variant of a T-bet protein can be created by introducing one or more nucleotide substitutions, additions or deletions into the nucleotide sequence of SEQ ID NO: 1 or 3 such that one or more amino acid substitutions, additions or deletions are introduced into the encoded protein. Mutations can be introduced into SEQ ID NO: 1 or 3 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in T-bet is preferably replaced with another amino acid residue from the same side chain family.

Alternatively, in another embodiment, mutations can be introduced randomly along all or part of the T-bet coding sequence, such as by saturation mutagenesis, and the resultant mutants can be screened for their ability to bind to DNA and/or activate transcription, to identify mutants that retain functional activity. Following mutagenesis, the encoded T-bet mutant protein can be expressed recombinantly in a host cell and the functional activity of the mutant protein can be determined using assays available in the art for assessing T-bet activity (e.g., by measuring the ability of the protein to bind to a T-box binding element present in DNA or by measuring the ability of the protein to modulate IL2 production.

Another aspect of the invention pertains to isolated nucleic acid molecules that are antisense to the coding strand of a T-bet mRNA or gene. An antisense nucleic acid of the invention can be complementary to an entire T-bet coding strand, or to only a portion thereof. In one embodiment, an antisense nucleic acid molecule is antisense to a coding region of the coding strand of a nucleotide sequence encoding T-bet that is unique to the T-bet family of proteins or which is unique to a T-bet sequence from a particular species. In another embodiment, the antisense nucleic acid molecule is antisense to a noncoding region of the coding strand of a nucleotide sequence encoding T-bet that is unique to T-bet family of proteins or which is unique to a T-bet sequence from a particular species. In preferred embodiments, an antisense molecule of the invention comprises at least about 700 contiguous nucleotides of the noncoding strand of SEQ ID NO: 1, more preferably at least 800, 1000, 1200, 1400, or 1600 contiguous nucleotides of the noncoding strand of SEQ ID NO: 1 or at least about 500 contiguous nucleotides of the noncoding strand of SEQ ID NO: 3, more preferably at least 600, 800, 1000, 1200, or 1400 contiguous nucleotides of the noncoding strand of SEQ ID NO: 3.

Given the coding strand sequences encoding T-bet disclosed herein (e.g., SEQ ID NOs: 1 and 3, antisense nucleic acids of the invention can be designed according to the rules of Watson and Crick base pairing. The antisense nucleic acid molecule may be complementary to the entire coding region of T-bet mRNA, or alternatively can be an oligonucleotide which is antisense to only a portion of the coding or noncoding region of T-bet mRNA. For example, the antisense oligonucleotide may be complementary to the region surrounding the translation start site of T-bet mRNA. An antisense oligonucleotide can be, for example, about 15, 20, 21, 22, 23, 24, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a T-bet-encoding nucleic acid can be designed based upon the nucleotide sequence of a T-bet gene disclosed herein. For example, a derivative of a Tetrahymena L-19 IVS RNA can be constructed in which the base sequence of the active site is complementary to the base sequence to be cleaved in a T-bet-encoding mRNA. See for example Cech et al. U.S. Pat. No. 4,987,071; and Cech et al. U.S. Pat. No. 5,116,742. Alternatively, T-bet mRNA can be used to select a catalytic RNA having a specific ribonuclease activity from a pool of RNA molecules. See for example Bartel, D. and Szostak, J. W. (1993) *Science* 261: 1411-1418.

In another embodiment, RNAi can be used to inhibit T-bet expression. RNA interference (RNAi is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA.

The antisense RNA strand of RNAi can be antisense to at least a portion of the coding region of T-bet or to at least a portion of the 5' or 3' untranslated region of the T-bet gene. In one embodiment, siRNA duplexes are composed of 21-nt sense and 21-nt antisense strands, paired in a manner to have a 2-nt 3' overhang. In one embodiment, siRNA sequences with TT in the overhang. The target region can be, e.g., 50 to 100 nt downstream of the start codon, 3'-UTRs may also be targeted. In one embodiment, a 23-nt sequence motif AA(N19)TT (N, any nucleotide) can be searched for and hits with between about 30-70% G/C-content can be selected. If no suitable sequences are found, the search is extended using the motif NA (N21). SiRNAs are preferably chemically synthesized using appropriately protected ribonucleoside phosphoramidites and a conventional DNA/RNA synthesizer. SiRNAs are also available commercially from, e.g., Dharmacon, Xeragon Inc, Proligo, and Ambion. In one embodiment one or more of the chemistries described above for use in antisense RNA can be employed.

Yet another aspect of the invention pertains to isolated nucleic acid molecules encoding T-bet fusion proteins. Such nucleic acid molecules, comprising at least a first nucleotide sequence encoding a T-bet protein, polypeptide or peptide operatively linked to a second nucleotide sequence encoding a non-T-bet protein, polypeptide or peptide, can be prepared by standard recombinant DNA techniques. T-bet fusion proteins are described in further detail below in subsection III.

II. Recombinant Expression Vectors and Host Cells

Another aspect of the invention pertains to vectors, preferably recombinant expression vectors, containing a nucleic acid encoding T-bet (or a portion thereof). The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., T-bet proteins, mutant forms of T-bet proteins, T-bet fusion proteins and the like).

The recombinant expression vectors of the invention can be designed for expression of T-bet protein in prokaryotic or eukaryotic cells. For example, T-bet can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors can serve one or more purposes: 1) to increase expression of recombinant protein; 2) to increase the solubility of the recombinant protein; 3) to aid in the purification of the recombinant protein by acting as a ligand in affinity purification; 4) to provide an epitope tag to aid in detection and/or purification of the protein; and/or 5) to provide a marker to aid in detection of the protein (e.g., a color marker using β-galactosidase fusions). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Recombinant proteins also can be expressed in eukaryotic cells as fusion proteins for the same purposes discussed above.

Examples of suitable inducible non-fusion *E. coli* expression vectors include pTrc (Amann et al. (1988) *Gene* 69:301-315) and pET 11d (Studier et al., *Gene Expression Technology: Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21 (DE3) or HMS 174(DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111-2118). Such alteration of nucleic acid sequences of the invention can be carried out by standard DNA synthesis techniques.

In another embodiment, the T-bet expression vector is a yeast expression vector. Examples of vectors for expression in yeast *S. cervisae* include pYepSec1 (Baldari. et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.).

Alternatively, T-bet can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156-2165) and the pVL series (Lucklow, V. A., and Summers, M. D., (1989) *Virology* 170:31-39).

In yet another embodiment, a nucleic acid of the invention is expressed in mammalian cells using a mammalian expression vector. Examples of mammalian expression vectors include pMex-NeoI, pCDM8 (Seed, B., (1987) *Nature* 329: 840) and pMT2PC (Kaufman et al. (1987), *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), the albumin promoter (liver-specific; Pinkert et al. (1987) *Genes Dev.* 1:268-277), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the a-fetoprotein promoter (Campes and Tilghman (1989) *Genes Dev.* 3:537-546).

Moreover, inducible regulatory systems for use in mammalian cells are known in the art, for example systems in which gene expression is regulated by heavy metal ions (see e.g., Mayo et al. (1982) *Cell* 29:99-108; Brinster et al. (1982) *Nature* 296:39-42; Searle et al. (1985) *Mol. Cell. Biol.* 5:1480-1489), heat shock (see e.g., Nouer et al. (1991) in *Heat Shock Response*, e.d. Nouer, L., CRC, Boca Raton, Fla., pp 167-220), hormones (see e.g., Lee et al. (1981) *Nature* 294:228-232; Hynes et al. (1981) *Proc. Natl. Acad. Sci. USA* 78:2038-2042; Klock et al. (1987) *Nature* 329:734-736; Israel & Kaufman (1989) *Nucl. Acids Res.* 17:2589-2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547-5551; Gossen, M. et al. (1995) *Science* 268:1766-1769; PCT Publication No. WO 94/29442; and PCT Publication No. WO 96/01313). Accordingly, in another embodiment, the invention provides a recombinant expression vector in which T-bet DNA is operatively linked to an inducible eukaryotic promoter, thereby allowing for inducible expression of T-bet protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to T-bet mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a vector, preferably a recombinant expression vector, of the invention has been introduced. A host cell may be any prokaryotic or eukaryotic cell. For example, T-bet protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to compounds, such as G418, hygromycin and methotrexate. Nucleic acid encoding a selectable marker may be introduced into a host cell on the same vector as that encoding T-bet or may be introduced on a separate vector. Cells stably transfected with the introduced nucleic acid can be identified by compound selection (e.g., cells that have incorporated the selectable marker gene will survive, while the other cells die).

A host cell of the invention, such as a prokaryotic or eukaryotic host cell in culture, can be used to produce (i.e., express) T-bet protein. Accordingly, the invention further provides methods for producing T-bet protein using the host cells of the invention. In one embodiment, the method comprises culturing the host cell of invention (into which a recombinant expression vector encoding T-bet has been introduced) in a suitable medium until T-bet is produced. In another embodiment, the method further comprises isolating T-bet from the medium or the host cell. In its native form the T-bet protein is an intracellular protein and, accordingly, recombinant T-bet protein can be expressed intracellularly in a recombinant host cell and then isolated from the host cell, e.g., by lysing the host cell and recovering the recombinant T-bet protein from the lysate. Alternatively, recombinant T-bet protein can be prepared as a extracellular protein by operatively linking a heterologous signal sequence to the amino-terminus of the protein such that the protein is secreted from the host cells. In this case, recombinant T-bet protein can be recovered from the culture medium in which the cells are cultured.

Certain host cells of the invention can also be used to produce nonhuman transgenic animals. For example, in one embodiment, a host cell of the invention is a fertilized oocyte or an embryonic stem cell into which T-bet-coding sequences have been introduced. Such host cells can then be used to create non-human transgenic animals in which exogenous T-bet sequences have been introduced into their genome or homologous recombinant animals in which endogenous T-bet sequences have been altered. Such animals are useful for studying the function and/or activity of T-bet and for identifying and/or evaluating modulators of T-bet activity. Accordingly, another aspect of the invention pertains to non-human transgenic animals which contain cells carrying a transgene encoding a T-bet protein or a portion of a T-bet protein. In a subembodiment, of the transgenic animals of the invention, the transgene alters an endogenous gene encoding an endogenous T-bet protein (e.g., homologous recombinant animals in which the endogenous T-bet gene has been functionally disrupted or "knocked out", or the nucleotide sequence of the endogenous T-bet gene has been mutated or the transcriptional regulatory region of the endogenous T-bet gene has been altered).

A transgenic animal of the invention can be created by introducing T-bet-encoding nucleic acid into the male pronuclei of a fertilized oocyte, e.g., by microinjection, and allowing the oocyte to develop in a pseudopregnant female foster animal. The T-bet nucleotide sequence of SEQ ID NO: 1 or 3 can be introduced as a transgene into the genome of a non-human animal. Intronic sequences and polyadenylation signals can also be included in the transgene to increase the efficiency of expression of the transgene. A tissue-specific regulatory sequence(s) can be operably linked to the T-bet transgene to direct expression of T-bet protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the T-bet transgene in its genome and/or expression of T-bet mRNA in tissues or cells of the animals. A transgenic founder animal can then be used to breed additional animals carrying the transgene. Moreover, transgenic animals carrying a transgene encoding T-bet can further be bred to other transgenic animals carrying other transgenes.

To create a homologous recombinant animal, a vector is prepared which contains at least a portion of a T-bet gene into which a deletion, addition or substitution has been introduced to thereby alter, e.g., functionally disrupt, the endogenous T-bet gene. In one embodiment, a homologous recombination vector is designed such that, upon homologous recombination, the endogenous T-bet gene is functionally disrupted (i.e., no longer encodes a functional protein; also referred to as a "knock out" vector). Alternatively, the vector can be designed such that, upon homologous recombination, the endogenous T-bet gene replaced by the T-bet gene. In the homologous recombination vector, the altered portion of the T-bet gene is flanked at its 5' and 3' ends by additional nucleic acid of the T-bet gene to allow for homologous recombination to occur between the exogenous T-bet gene carried by the vector and an endogenous T-bet gene in an embryonic stem cell. The additional flanking T-bet nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced T-bet gene has homologously recombined with the endogenous T-bet gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025-2029; and Fukushige, S. and Sauer, B. (1992) *Proc. Natl. Acad. Sci. USA* 89:7905-7909) and the FLP recombinase-FRT target system (e.g., as described in Dang, D. T. and Perrimon, N. (1992) *Dev. Genet.* 13:367-375; and Fiering, S. et al. (1993) *Proc. Natl. Acad. Sci. USA* 90:8469-8473). Tetracycline-regulated inducible homologous recombination systems, such as described in PCT Publication No. WO 94/29442 and PCT Publication No. WO 96/01313, also can be used.

In another embodiment, transgenic animals can be made in which T-bet is expressed in all T cells, e.g., using the CD4 enhancer (Zheng, W-P. & Flavell, R. A. 1997. *Cell* 89, 587). Recent work suggests the CD2 enhancer can also be used. In fact, it is more powerful in achieving high level expression in T cells, expression is not variegated and transgene expression is copy number-dependent (Zhumabekov, T., et al. 1995. *J. Immunol. Meth.* 185, 133; Sharp, L. L., et al. 1997. *Immunity* 7, 609). Mice with high level expression of T-bet RNA (using the human growth hormone intron as a probe to distinguish transgene driven T-bet RNA from endogenous T-bet) can be identified by screening adequate numbers of founders.

In another approach, a dominant repressor transgenic can be created. For example, a dominant-repressor T-bet can be made by using the proximal lck enhancer (Alberola-Ila, J., et al. 1996 *J. Exp. Med.* 184, 9) driving a fusion of T-bet and engrailed can be made (Taylor, D., 1996. *Genes Dev.* 10, 2732; Li, J., Thurm, H., et al. 1997. *Proc. Natl. Acad. Sci. USA* 94, 10885). This construct specifically represses T-bet transactivation of a multimerized T-bet reporter and does not affect NFAT-dependent reporter transactivation.

Alternatively, null mutations can be generated by targeted mutagenesis in ES cells (Ranger, A. M., et al. 1998. *Nature* 392, 186; Hodge, M. R., et al. 1996. *Immunity* 4:1., 144; Grusby, M. J., et al. 1991. *Science* 253, 1417; Reimold, A. M., et al. 1996. *Nature* 379: 262; Kaplan, M. H., 1996. *Immunity:* 313; Kaplan, M. H., et al. 1996. *Nature* 382, 174; Smiley, S. T., et al. 1997. *Science* 275, 977). For example using techniques which are known in the art, a genomic T-bet clone can be isolated from a genomic library, the intron-exon organization delineated, and a targeting construct in the cre-lox vector (see discussion below) created which should delete the first exon and 450 bp of upstream promoter sequence. This construct can be electroporated into an ES cell line, and double compound resistant (e.g., neomycin, gancyclovir) clones identified by Southern blot analysis. Clones bearing homologous recombinant events in the T-bet locus can then be identified and injected into blastocysts obtained from day 3.5 BALB/c pregnant mice. Chimeric mice can then be produced and mated to wildtype BALB/c mice to generate germline transmission of the disrupted T-bet gene.

In another embodiment, implantation into RAG2-deficient blastocysts (Chen, J., et al. 1993. *Proc. Natl. Acad Sci. USA* 90, 4528) or the cre-lox inducible deletion approach can be used to develop mice that are lacking T-bet only in the immune system. For example, the targeting construct can be made in the cre-lox vector. The blastocyst complementation system has been used to study NFATc, an embryonic lethal phenotype (Ranger, A. M., et al. 1998. *Immunity* 8:125). This approach requires disrupting the T-bet gene on both chromosomes in ES cells, which can be accomplished, e.g., by using a mutant neomycin gene and raising the concentration of G418 in the ES cultures, as described (Chen, J., 1993. *Proc. Natl. Acad. Sci. USA* 90;4528) or by flanking the neo gene with cre-lox sites. To disrupt the second allele, the neomycin gene can be deleted by transfecting the ES clone with the cre recombinase, and then the ES clone can be retransfected with the same targeting construct to select clones with T-bet deletions on both alleles. A third transfection with cre-recombinase yields the desired doubly-deficient ES cells. Such doubly targeted ES cells are then implanted into RAG2 blastocysts and the lymphoid organs of the chimeric mice thus generated will be entirely colonized by the transferred ES cells. This allows assessment of the effect of the absence of T-bet on cells of the lymphoid system without affecting other organ systems where the absence of T-bet might cause lethality.

The conditional ablation approach employing the cre-lox system can also be used. Briefly, a targeting construct is generated in which lox recombination sequences are placed in intronic regions flanking the exons to be deleted. This construct is then transfected into ES cells and mutant mice are generated as above. The resulting mutant mice are then mated to mice transgenic for the cre recombinase driven by an inducible promoter. When cre is expressed, it induces recombination between the introduced lox sites in the T-bet gene, thus effectively disrupting gene function. The key feature of this approach is that gene disruption can be induced in the adult animal at will by activating the cre recombinase.

A tissue-specific promoter can be used to avoid abnormalities in organs outside the immune system. The cre-expressing transgene may be driven by an inducible promoter. Several inducible systems are now being used in cre-lox recombination strategies, the most common being the tetracycline and ecdysone systems. A tissue-specific inducible promoter can be used if there is embryonic lethality in the T-bet null mouse.

An alternative approach is to generate a transgenic mouse harboring a regulated T-bet gene (for example using the tetracycline off promoter; e.g., St-Onge, et al. 1996. *Nuc. Acid Res.* 24, 3875-3877) and then breed this transgenic to the T-bet deficient mouse. This approach permits creation of mice with normal T-bet function; tetracycline can be administered to adult animals to induce disruption of T-bet function in peripheral T cells, and then the effect of T-bet deficiency can be examined over time. Repeated cycles of provision and then removal of compound (tetracycline) permits turning the T-bet gene on and off at will.

III. Isolated T-Bet Proteins and Anti-T-Bet Antibodies

Another aspect of the invention pertains to isolated T-bet proteins. Preferably, the T-bet protein comprises the amino acid sequence encoded by SEQ ID NO:1 or 3. In another preferred embodiment, the protein comprises the amino acid sequence of SEQ ID NO: 2 or 4. In other embodiments, the protein has at least 60% amino acid identity, more preferably 70% amino acid identity, more preferably 80%, and even more preferably, 90% or 95% amino acid identity with the amino acid sequence shown in SEQ ID NO: 2 or 4.

In other embodiments, the invention provides isolated portions of the T-bet protein. For example, the invention further encompasses an amino-terminal portion of T-bet that includes a T-box domain. In various embodiments, this amino terminal portion encompasses at least amino acids 138-327 of human T-bet or at least amino acids 137-326 of mouse T-bet. Another isolated portion of T-bet provided by the invention is a portion encompassing a tyrosine phosphorylation site. This portion comprises at least about 20, at least about 50, at least about 100, or at least about 200 amino acids of T-bet and includes at least amino acids Tyr 76, Tyr 119, and/or Tyr 531 of human T-bet or amino acids Tyr 525 of murine T-bet. Yet another isolated portion of T-bet provided herein is a portion encompassing a nuclear localization sequence shown in amino acids 498-501 of human T-bet or 493-496 of murine T-bet. Another isolated portion of T-bet provided herein is a portion encompassing a serine phosphorylation site. This portion comprises at least about 20, at least about 50, at least about 100, or at least about 200 amino acids of T-bet and includes at least amino acid Ser 508 of human T-bet or amino acid Ser 507 of murine T-bet.

T-bet proteins of the invention are preferably produced by recombinant DNA techniques. For example, a nucleic acid molecule encoding the protein is cloned into an expression vector (as described above), the expression vector is introduced into a host cell (as described above) and the T-bet protein is expressed in the host cell. The T-bet protein can then be isolated from the cells by an appropriate purification scheme using standard protein purification techniques. Alternative to recombinant expression, a T-bet polypeptide can be synthesized chemically using standard peptide synthesis techniques. Moreover, native T-bet protein can be isolated from cells (e.g., from T cells), for example by immunoprecipitation using an anti-T-bet antibody.

The present invention also pertains to variants of the T-bet proteins which function as either T-bet agonists (mimetics) or as T-bet antagonists. Variants of the T-bet proteins can be generated by mutagenesis, e.g., discrete point mutation or truncation of a T-bet protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the T-bet protein. In one embodiment, the invention pertains to derivatives of T-bet which may be formed by modifying at least one amino acid residue of T-bet by oxidation, reduction, or other derivatization processes known in the art.

In one embodiment, variants of a T-bet protein which function as either T-bet agonists (mimetics) or as T-bet antagonists can be identified by screening combinatorial libraries of mutants, e.g., truncation mutants, of a T-bet protein for T-bet protein agonist or antagonist activity. In one embodiment, a variegated library of T-bet variants is generated by combinatorial mutagenesis at the nucleic acid level and is encoded by a variegated gene library. A variegated library of T-bet variants can be produced by, for example, enzymatically ligating a mixture of synthetic oligonucleotides into gene sequences such that a degenerate set of potential T-bet sequences is expressible as individual polypeptides, or alternatively, as a set of larger fusion proteins (e.g., for phage display) containing the set of T-bet sequences therein. There are a variety of methods which can be used to produce libraries of potential T-bet variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential T-bet sequences. Methods for synthesizing degenerate oligonucleotides are known in the art (see, e.g., Narang, S. A., 1983, *Tetrahedron* 39:3; Itakura et al., 1984, *Annu. Rev. Biochem.* 53:323; Itakura et al., 1984, *Science* 198:1056; Ike et al., 1983, *Nucleic Acid Res.* 11:477).

In addition, libraries of fragments of a T-bet protein coding sequence can be used to generate a variegated population of T-bet fragments for screening and subsequent selection of variants of a T-bet protein. In one embodiment, a library of coding sequence fragments can be generated by treating a double stranded PCR fragment of a T-bet coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the T-bet protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of T-bet proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify T-bet variants (Arkin and Yourvan, 1992, *Proc. Natl. Acad. Sci. USA* 89:7811-7815; Delgrave et al., 1993, *Protein Engineering* 6(3):327-331).

The invention also provides T-bet fusion proteins. As used herein, a T-bet "fusion protein" comprises a T-bet polypeptide operatively linked to a polypeptide other than T-bet. A "T-bet polypeptide" refers to a polypeptide having an amino acid sequence corresponding to T-bet protein, or a peptide fragment thereof which is unique to T-bet protein whereas a "polypeptide other than T-bet" refers to a polypeptide having an amino acid sequence corresponding to another protein. Within the fusion protein, the term "operatively linked" is intended to indicate that the T-bet polypeptide and the other polypeptide are fused in-frame to each other. The other polypeptide may be fused to the N-terminus or C-terminus of the T-bet polypeptide. For example, in one embodiment, the fusion protein is a GST-T-bet fusion protein in which the T-bet sequences are fused to the C-terminus of the GST sequences. In another embodiment, the fusion protein is a T-bet-HA fusion protein in which the T-bet nucleotide sequence is inserted in a vector such as pCEP4-HA vector (Herrscher, R. F. et al. (1995) *Genes Dev.* 9:3067-3082) such that the T-bet sequences are fused in frame to an influenza hemagglutinin epitope tag. Such fusion proteins can facilitate the purification of recombinant T-bet.

Preferably, a T-bet fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A T-bet-encoding nucleic acid can be cloned into such an expression vector such that the fusion moiety is linked in-frame to the T-bet protein.

An isolated T-bet protein, or fragment thereof, can be used as an immunogen to generate antibodies that bind specifically to T-bet using standard techniques for polyclonal and monoclonal antibody preparation. The T-bet protein can be used to generate antibodies. For example, polyclonal antisera, can be produced in rabbits using full-length recombinant bacterially produced T-bet as the immunogen. This same immunogen can be used to produce mAb by immunizing mice and removing spleen cells from the immunized mice. Spleen cells from mice mounting an immune response to T-bet can be fused to myeloma cells, e.g., SP2/O-Ag14 myeloma. As described in the appended examples, this methods were used to make polyclonal and monoclonal antibodies which bind to T-bet. In one embodiment, the antibodies can be produced in an animal that does not express T-bet, such as a T-bet knock-out animal. In another embodiment, the antibodies can be generated in a non-human animal having a specific genetic background, e.g., as achieved by backcrossing.

Alternatively, an antigenic peptide fragment of T-bet can be used as the immunogen. An antigenic peptide fragment of T-bet typically comprises at least 8 amino acid residues of the amino acid sequence shown in SEQ ID NO: 2 or 4 and encompasses an epitope of T-bet such that an antibody raised against the peptide forms a specific immune complex with T-bet. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of T-bet that are located on the surface of the protein, e.g., hydrophilic regions, and that are unique to T-bet. In one embodiment such epitopes can be specific for T-bet proteins from one species, such as mouse or human (i.e., an antigenic peptide that spans a region of T-bet that is not conserved across species is used as immunogen; such non conserved residues can be determined using an alignment such as that provided herein). A standard hydrophobicity analysis of the T-bet protein can be performed to identify hydrophilic regions.

A T-bet immunogen typically is used to prepare antibodies by immunizing a suitable subject, (e.g., rabbit, goat, mouse or other mammal) with the immunogen. An appropriate immunogenic preparation can contain, for examples, recombinantly expressed T-bet protein or a chemically synthesized T-bet peptide. The preparation can further include an adjuvant, such as Freund's complete or incomplete adjuvant, or similar immunostimulatory agent. Immunization of a suitable subject with an immunogenic T-bet preparation induces a polyclonal anti-T-bet antibody response.

Accordingly, another aspect of the invention pertains to anti-T-bet antibodies. Polyclonal anti-T-bet antibodies can be prepared as described above by immunizing a suitable subject with a T-bet immunogen. The anti-T-bet antibody titer in the immunized subject can be monitored over time by standard techniques, such as with an enzyme linked immunosorbent assay (ELISA) using immobilized T-bet. If desired, the antibody molecules directed against T-bet can be isolated from the mammal (e.g., from the blood) and further purified by well known techniques, such as protein A chromatography to obtain the IgG fraction. At an appropriate time after immunization, e.g., when the anti-T-bet antibody titers are highest, antibody-producing cells can be obtained from the subject and used to prepare monoclonal antibodies by standard techniques, such as the hybridoma technique originally described by Kohler and Milstein (1975, *Nature* 256:495-497) (see also, Brown et al. (1981) *J. Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.*, 3:231-36). Briefly, an immortal cell line (typically a myeloma) is fused to lymphocytes (typically splenocytes) from a mammal immunized with a T-bet immunogen as described above, and the culture supernatants of the resulting hybridoma cells are screened to identify a hybridoma producing a monoclonal antibody that binds specifically to T-bet.

Any of the many well known protocols used for fusing lymphocytes and immortalized cell lines can be applied for the purpose of generating an anti-T-bet monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind T-bet, e.g., using a standard ELISA assay.

Using such methods several antibodies to T-bet have been generated. Both monoclonal and polyclonal antibodies were generated against full-length recombinant bacterially produced T-bet protein. The 3D10 antibody is of the IgG subtype and the 4B 10 antibody was produced by fusion of mouse spleen cells to the SP2/0-Ag14 myeloma and is of the IgG subtype. The 39D antibody recognizes both human and murine T-bet.

Alternative to preparing monoclonal antibody-secreting hybridomas, a monoclonal anti-T-bet antibody can be identified and isolated by screening a recombinant combinatorial immunoglobulin library (e.g., an antibody phage display library) with T-bet to thereby isolate immunoglobulin library members that bind T-bet. Kits for generating and screening phage display libraries are commercially available (e.g., the *Pharmacia Recombinant Phage Antibody System*, Catalog No. 27-9400-01; and the *Stratagene SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clarkson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; Barbas et al. (1991) *PNAS* 88:7978-7982; and McCafferty et al. *Nature* (1990) 348:552-554.

Additionally, recombinant anti-T-bet antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *PNAS* 84:3439-3443; Liu et al. (1987) *J. Immunol.* 139:3521-3526; Sun et al. (1987) *PNAS* 84:214-218; Nishimura et al. (1987) *Canc. Res.* 47:999-1005; Wood et al. (1985) *Nature* 314:446-449; and Shaw et al. (1988) *J. Natl Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In another embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140. Other techniques are known in the art.

An anti-T-bet antibody (e.g., monoclonal antibody) can be used to isolate T-bet by standard techniques, such as affinity chromatography or immunoprecipitation. An anti-T-bet antibody can facilitate the purification of natural T-bet from cells and of recombinantly produced T-bet expressed in host cells. Moreover, an anti-T-bet antibody can be used to detect T-bet protein (e.g., in a cellular lysate or cell supernatant). Detection may be facilitated by coupling (i.e., physically linking) the antibody to a detectable substance. Accordingly, in one embodiment, an anti-T-bet antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidinibiotin and avidinibiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S or $^{3}$H.

Yet another aspect of the invention pertains to anti-T-bet antibodies that are obtainable by a process comprising:

(a) immunizing an animal with an immunogenic T-bet protein, or an immunogenic portion thereof unique to T-bet protein; and (b) isolating from the animal antibodies that specifically bind to a T-bet protein.

Methods for immunization and recovery of the specific anti-T-bet antibodies are described further above.

In yet another aspect, the invention pertains to T-bet intrabodies. Intrabodies are intracellularly expressed antibody constructs, usually single-chain Fv (scFv) antibodies directed against a target inside a cell, e.g. an intracellular protein such as T-bet (Graus-Porta, D. et al. (1995) Mol. Cell Biol. 15(1): 182-91). For example, an intrabody (e.g., and scFv) can contain the variable region of the heavy and the light chain, linked by a flexible linker and expressed from a single gene. The variable domains of the heavy and the light chain contain the complementarity determining regions (CDRs) of the parent antibody, i.e., the main antigen binding domains, which determine the specificity of the scFvs. The scFv gene can be transferred into cells, where scFv protein expression can modulate the properties of its target, e.g., T-bet. Accordingly, in one embodiment, the invention provides a method for using such T-bet intrabodies to prevent T-bet activity in cells, for example, in an in vivo or ex vivo approach, for which the cells are modified to express such intrabodies. In a particular embodiment, the T-bet intrabodies of the invention can be used to directly inhibit T-bet activity. In another embodiment, the T-bet intrabodies can be used to inhibit the interaction of T-bet and a protein with which T-bet interacts. Thus, the T-bet intrabodies of the invention are useful in modulating signaling pathways in which T-bet is involved.

The T-bet intrabodies can be prepared using techniques known in the art. For example, phage display technology can be used to isolate scFvs from libraries (Lowman, H B et al. (1991) *Biochemistry* 30(10): 832-8). To select scFvs binding to a particular antigen, the scFvs are fused to a coat protein, typically pIII (g3p) of filamentous M13 phage. An scFv on the phage that binds an immobilized antigen is enriched during consecutive cycles of binding, elution and amplification. In another example, ribosome display can used to prepare T-bet intrabodies (Hanes, J. et al. (1997) *Proc. Natl. Acad. Sci.* 94(1): 937-44). Ribosome display is an in vitro method that links the peptide directly to the genetic information (mRNA). An scFv cDNA library is expressed in vitro using a transcription translation system. The translated ScFvs are stalled to the ribosome linked to the encoding mRNA. The scFv is then bound to the immobilized antigen and unspecific ribosome complexes are removed by extensive washes. The remaining complexes are eluted and the RNA is isolated, reverse transcribed to cDNA and subsequently re-amplified by PCR. In yet another example, a Protein Fragment Complementation Assay (PCA) can be used to prepare T-bet intrabodies of the invention (Pelletier, J N et al. (1998) *Proc. Natl. Acad. Sci.* 95(12): 141-6.) This is a cellular selection procedure based on the complementation of a mutant dihydrofolate reductase (DHFR) in *E. coli* by the mouse protein (mDHFR). The murine DHFR is dissected into two parts, which are expressed as fusion proteins with potentially interacting peptides. The interaction of the fusion proteins restores the enzymatic activity of mDHFR, and thus bacterial proliferation. Only a specific interaction of antibody and antigen allows the functional complementation of DHFR which makes the system amenable for the selection of scFvs (Mossner, E. et al. (2001) *J Mol. Biol.* 308: 115-22).

V. Methods of the Invention

A. Detection of T-Bet Compositions

Another aspect of the invention pertains to methods of using the various T-bet compositions of the invention. For example, the invention provides a method for detecting the presence of T-bet activity in a biological sample. The method involves contacting the biological sample with an agent capable of detecting T-bet activity, such as T-bet protein or T-bet mRNA, such that the presence of T-bet activity is detected in the biological sample.

A preferred agent for detecting T-bet mRNA is a labeled nucleic acid probe capable of specifically hybridizing to T-bet mRNA. The nucleic acid probe can be, for example, the T-bet DNA of SEQ ID NO: 1 or 3, such as an oligonucleotide of at least about 500, 600, 800, 900, 1000, 1200, 1400, or 1600 nucleotides in length and which specifically hybridizes under stringent conditions to T-bet mRNA.

A preferred agent for detecting T-bet protein is a labeled antibody capable of binding to T-bet protein. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids. For example, techniques for detection of T-bet mRNA include Northern hybridizations and in situ hybridizations. Techniques for detection of T-bet protein include enzyme linked immunosorbent assays (ELISAs), Western blots, immunoprecipitations and immunofluorescence.

B. Screening Methods

The invention further provides methods for identifying compounds, i.e., candidate or test compounds or agents (e.g., peptidomimetics, small molecules or other drugs) that modulate, e.g., increase or decrease IL2 production. Modulators of IL2 can be known (e.g., dominant negative inhibitors of T-bet activity, antisense T-bet, intracellular antibodies that interfere with T-bet activity, peptide inhibitors derived from T-bet or Tbet nucleic acid or protein molecules) or can be identified using the methods described herein.

For example, in one embodiment, molecules which modulate the interaction, e.g., binding, of T-bet to a kinase, e.g., a serine-threonine kinase, molecule can be identified. For example, a kinase, e.g., a serine-threonine kinase, mediates the interaction of T-bet with RelA, and therefore, any of these molecules can be used in the subject screening assays. Although the specific embodiments described below in this section and in other sections may list one of these molecules as an example, other molecules that interact with and/or are involved in a signal transduction pathway involving T-bet can also be used in the subject screening assays.

In one embodiment, the ability of a compound to directly modulate, e.g., increase or stabilize, or decrease or destabilize, the formation of a complex between T-bet and a kinase, e.g., a serine-threonine kinase, e.g., a CKI or GSK-3 kinase, is measured. In other embodiments, the post-translational modification (e.g., phosphorylation) of T-bet, or the expression and/or activity of a kinase that phosphorylates T-bet or T-bet is measured in an indicator composition using a screening assay of the invention. In yet another embodiment, the formation of a complex between RelA and T-bet is measured. In another embodiment, IL2 cytokine production is measured.

The indicator composition can be a cell that expresses the T-bet protein or a molecule that interacts with T-bet or a molecule in a signal transduction pathway involving T-bet, for example, a cell that naturally expresses or, more preferably, a cell that has been engineered to express the protein by introducing into the cell an expression vector encoding the protein. Preferably, the cell is a mammalian cell, e.g., a human cell. In one embodiment, the cell is a T cell. In one preferred embodiment, the cell is committed to a T cell lineage. In another preferred embodiment, the cell is not yet committed to a T cell lineage. In another embodiment, the cell is a B cell. In yet another embodiment, the cell is a NK cell. Alternatively, the indicator composition can be a cell-free composition that includes the protein (e.g., a cell extract or a composition that includes, e.g., either purified natural or recombinant protein).

The ability of a compound to modulate IL2 production can be measured, e.g., by measuring the production of IL-2 mRNA, by, for example, quantitative RT-PCR, and/or measuring IL-2 protein production using, for example Western blot analysis.

In one embodiment, the invention provides methods for identifying modulators, i.e., candidate or test compounds or agents (e.g., enzymes, peptides, peptidomimetics, small molecules, ribozymes, or T-bet antisense molecules) which bind to T-bet polypeptides; have a stimulatory or inhibitory effect on T-bet expression; T-bet processing; T-bet post-translational modification (e.g., glycosylation, ubiquitinization, or phosphorylation); or T-bet activity; or have a stimulatory or inhibitory effect on the expression, processing or activity of a T-bet binding partner or target molecule.

In one preferred embodiment, the invention features a method for identifying a compound which modulates IL2 production comprising contacting in the presence of the compound, T-bet and a serine-threonine kinase molecule under conditions which allow interaction of the kinase molecule with T-bet; and detecting the interaction of T-bet and the kinase molecule, wherein the ability of the compound to increase IL2 production is indicated by a decrease in the interaction as compared to the amount of interaction in the absence of the compound and the ability of the compound to decrease IL2 production is indicated by a increase in the interaction as compared to the amount of interaction in the absence of the compound.

In another preferred embodiment, the invention features a method of identifying compounds useful in modulating IL2 production comprising, a) providing an indicator composition comprising T-bet, RelA, and an IL-2 regulatory region;

b) contacting the indicator composition with each member of a library of test compounds;

c) selecting from the library of test compounds a compound of interest that decreases the T-bet-mediated interaction of RelA and the IL-2 regulatory region to thereby identify a compound that modulates IL-2 production, wherein the ability of the compound to increase IL-2 production is indicated by a decrease in the interaction as compared to the amount of interaction in the absence of the compound, and the ability of the compound to decrease IL-2 production is indicated by a increase in the interaction as compared to the amount of interaction in the absence of the compound.

In yet another preferred embodiment, the invention features a method for identifying a compound which modulates the interaction of RelA and an IL-2 regulatory region in a T cell, comprising contacting in the presence of the compound and T-bet, RelA and the IL-2 regulatory region under conditions which allow T-bet-mediated binding of RelA to the IL-2 regulatory region to form a complex; and detecting the formation of a complex of RelA and the IL-2 regulatory region in which the ability of the compound to inhibit interaction between RelA and the IL-2 regulatory region in the presence of T-bet and the compound is indicated by a decrease in complex formation as compared to the amount of complex formed in the absence of T-bet and the compound.

In yet another preferred embodiment, the invention features a method of increasing IL-2 cytokine production by a T cell, comprising contacting the cell with an agent that downmodulates the kinase-mediated binding of T-bet and RelA in the T cell, such that IL-2 production by the T cell is increased.

Compounds identified using the assays described herein may be useful for treating disorders associated with aberrant T-bet expression, processing, post-translational modification, or activity, modulation of T cell lineage commitment, modulating the production of cytokines, modulating TGF-β mediated signaling, modulating the Jak1/STAT-1 pathway, modulating IgG class switching and modulating B lymphocyte function.

Conditions that may benefit from upmodulation of IL2 production by decreasing the formation and/or stability of a complex between T-bet and RelA and/or a kinase, e.g., a serine-threonine kinase, include disorders certain immune deficiency disorders or disorders in which Th1 cytokine production may be too high.

Conditions that may benefit from downmodulation of IL2 production by increasing the formation and/or stability of a complex between T-bet and RelA and/or a kinase, e.g., a serine-threonine kinase, include autoimmune disorders including: diabetes mellitus, rheumatoid arthritis, juvenile rheumatoid arthritis, osteoarthritis, psoriatic arthritis, multiple sclerosis, myasthenia gravis, systemic lupus erythematosis, autoimmune thyroiditis, atopic dermatitis and eczematous dermatitis, psoriasis, Sjögren's Syndrome, alopecia areata, allergic responses due to arthropod bite reactions, Crohn's disease, aphthous ulcer, iritis, conjunctivitis, keratoconjunctivitis, ulcerative colitis, allergic asthma, cutaneous lupus erythematosus, scleroderma, vaginitis, proctitis, compound eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, experimental allergic encephalomyelitis (EAE), interstitial lung fibrosis, Hodgkin's disease, Graft-versus-Host reaction, multiple sclerosis, type-1 diabetes, lepromatous leprosy, AIDS, immunodeficiency syndrome, severe burn traumas, and allogenic bone marrow transplantation.

Conditions that may benefit from upmodulation of IL-2 production by decreasing the formation and/or stability of a complex between T-bet and RelA and/or a kinase, e.g., a serine-threonine kinase, include, for example various types of cancer, such as those cancers that are refractory to conventional treatment. For example, combination therapy with systemically administered IL-2 has resulted in long-term remissions in 30 percent of patients with metastatic renal cell carcinoma, for which there is no standard treatment. Objective and long-lived clinical responses have been documented also in a proportion of patients with melanoma or acute myeloid leukemia.

The subject screening assays can be performed in the presence or absence of other agents. For example, the subject assays can be performed in the presence various agents that modulate the activation state of the cell being screened. For example, in one embodiment, agents that transduce signals via the T cell receptor are included. In another embodiment, a cytokine or an antibody to a cytokine receptor is included. In another embodiment, an agent that inhibits phosphorylation can also be included.

In another aspect, the invention pertains to a combination of two or more of the assays described herein. For example, a modulating agent can be identified using a cell-based or a cell-free assay, and the ability of the agent to modulate IL2 production can be confirmed in vivo, e.g., in an animal.

Moreover, a modulator of IL2 production identified as described herein (e.g., a dominant negative T-bet molecule, a T-bet nucleic acid or polypeptide molecule, an antisense T-bet nucleic acid molecule, a T-bet-specific antibody, or a small molecule) can be used in an animal model to determine the efficacy, toxicity, or side effects of treatment with such a modulator. Alternatively, a modulator identified as described herein can be used in an animal model to determine the mechanism of action of such a modulator.

In another embodiment, it will be understood that similar screening assays can be used to identify compounds that indirectly modulate a T-bet expression and/or activity, e.g., by performing screening assays such as those described above, but employing molecules with which T-bet interacts, i.e., molecules that act either upstream or downstream of T-bet in a signal transduction pathway, such as a kinase.

Accordingly, as described below, the invention provides a screening assay for identifying compounds that modulate the interaction of T-bet and a T-box binding region (e.g., a cytokine gene regulatory region, such as an IL-2) or the ability of RelA (or a complex between T-bet and RelA and a kinase) to bind to DNA. Assays are known in the art that detect the interaction of a DNA binding protein with a target DNA sequence (e.g., electrophoretic mobility shift assays, DNAse I footprinting assays, chromatin immunoprecipitation (ChIP assays), and the like). By performing such assays in the presence and absence of test compounds, these assays can be used to identify compounds that modulate (e.g., inhibit or enhance) the interaction of the DNA binding protein with its target DNA sequence.

The cell based and cell free assays of the invention are described in more detail below.

i. Cell Based Assays

The indicator compositions of the invention can be a cell that expresses a T-bet polypeptide (and/or one or more non-T-bet polypeptides such as a kinase), for example, a cell that naturally expresses endogenous T-bet or, more preferably, a cell that has been engineered to express an exogenous T-bet polypeptide by introducing into the cell an expression vector encoding the polypeptide. Alternatively, the indicator composition can be a cell-free composition that includes T-bet and/or one or more non-T-bet polypeptides such as a kinase (e.g., a cell extract from a T-bet-expressing cell or a composition that includes purified T-bet, either natural or recombinant polypeptide).

Compounds that modulate IL2 production can be identified using various "read-outs."

For example, an indicator cell can be transfected with a T-bet expression vector, incubated in the presence and in the absence of a test compound, and the effect of the compound on the expression of the molecule or on a biological response regulated by T-bet can be determined. The biological activities of T-bet include activities determined in vivo, or in vitro, according to standard techniques. A T-bet activity can be a direct activity, such as an association of T-bet with a T-bet-target molecule (e.g., a nucleic acid molecule to which T-bet binds such as the transcriptional regulatory region of a cytokine gene or a polypeptide, e.g., a kinase or RelA). Alternatively, a T-bet activity is a downstream activity, such as a cellular signaling activity occurring downstream of the interaction of the T-bet polypeptide with a T-bet target molecule or a biological effect occurring as a result of the signaling cascade triggered by that interaction. For example, biological activities of T-bet described herein include: modulation of T cell lineage commitment, e.g., directly modulate, modulating the production of cytokines, modulating TGF-β mediated signaling, modulating the Jak1/STAT-1 pathway, modulating IgG class switching and modulating B lymphocyte function. The various biological activities of T-bet can be measured using techniques that are known in the art. Exemplary techniques are described in more detail in the Examples.

To determine whether a test compound modulates T-bet expression, in vitro transcriptional assays can be performed. To perform such an assay, the full length promoter and enhancer of T-bet can be operably linked to a reporter gene such as chloramphenicol acetyltransferase (CAT) or luciferase and introduced into host cells.

As used interchangeably herein, the terms "operably linked" and "operatively linked" are intended to mean that the nucleotide sequence is linked to a regulatory sequence in a manner which allows expression of the nucleotide sequence in a host cell (or by a cell extract). Regulatory sequences are art-recognized and can be selected to direct expression of the desired polypeptide in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of polypeptide desired to be expressed.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

A variety of cell types are suitable for use as indicator cells in the screening assay. Preferably a cell line is used which does not normally express T-bet, such as a Th2 cell clone or a cell from a knock out animal. Nonlymphoid cell lines can also be used as indicator cells, such as the HepG2 hepatoma cell line. Yeast cells also can be used as indicator cells.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell.

In one embodiment, the level of expression of the reporter gene in the indicator cell in the presence of the test compound is higher than the level of expression of the reporter gene in the indicator cell in the absence of the test compound and the test compound is identified as a compound that stimulates the expression of T-bet. In another embodiment, the level of expression of the reporter gene in the indicator cell in the presence of the test compound is lower than the level of expression of the reporter gene in the indicator cell in the absence of the test compound and the test compound is identified as a compound that inhibits the expression of T-bet.

In one embodiment, the invention provides methods for identifying compounds that modulate cellular responses in which T-bet is involved.

The ability of a test compound to modulate T-bet binding to a target molecule or to bind to T-bet can also be determined. Determining the ability of the test compound to modulate T-bet binding to a target molecule (e.g., a binding partner) can be accomplished, for example, by coupling the T-bet target molecule with a radioisotope, enzymatic or fluorescent label such that binding of the T-bet target molecule to T-bet can be determined by detecting the labeled T-bet target molecule in a complex. Alternatively, T-bet can be coupled with a radioisotope, enzymatic or fluorescent label to monitor the ability of a test compound to modulate T-bet binding to a T-bet target molecule in a complex. Determining the ability of the test compound to bind T-bet can be accomplished, for example, by coupling the compound with a radioisotope, enzymatic or fluorescent label such that binding of the compound to T-bet can be determined by detecting the labeled T-bet compound in a complex. For example, T-bet targets can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to interact with T-bet without the labeling of any of the interactants. For example, a microphysiometer can be used to detect the interaction of a compound with T-bet without the labeling of either the compound or the T-bet (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and T-bet.

In another embodiment, a different (i.e., non-T-bet) molecule acting in a pathway involving T-bet that acts upstream or downstream of T-bet can be included in an indicator composition for use in a screening assay. Compounds identified in a screening assay employing such a molecule would also be useful in modulating T-bet activity, albeit indirectly. An exemplary molecule with which T-bet interacts includes a kinase.

The cells of the invention can express endogenous T-bet (or another polypeptide in a signaling pathway involving T-bet) or may be engineered to do so. A cell that has been engineered to express the T-bet polypeptide or a non T-bet polypeptide which acts upstream or downstream of T-bet can be produced by introducing into the cell an expression vector encoding the T-bet polypeptide or a non T-bet polypeptide which acts upstream or downstream of T-bet.

Recombinant expression vectors that can be used for expression of T-bet polypeptide or a non T-bet polypeptide which acts upstream or downstream of T-bet in the indicator cell are known in the art. In one embodiment, within the expression vector the T-bet-coding sequences are operatively linked to regulatory sequences that allow for inducible or constitutive expression of T-bet in the indicator cell (e.g., viral regulatory sequences, such as a cytomegalovirus promoter/enhancer, can be used). Use of a recombinant expression vector that allows for inducible or constitutive expression of T-bet in the indicator cell is preferred for identification of compounds that enhance or inhibit the activity of T-bet. In an alternative embodiment, within the expression vector the T-bet-coding sequences are operatively linked to regulatory sequences of the endogenous T-bet gene (i.e., the promoter regulatory region derived from the endogenous T-bet gene). Use of a recombinant expression vector in which T-bet expression is controlled by the endogenous regulatory sequences is preferred for identification of compounds that enhance or inhibit the transcriptional expression of T-bet.

T-bet was isolated in a yeast one hybrid screening assay based on its ability to bind to the IL-2 promoter. Accordingly, in one embodiment, a method of the invention utilizes a reporter gene construct containing this region of the proximal IL-2 promoter, most preferably nucleotides -240 to -220 of the IL-2 promoter. Other sequences that can be employed include: , the human IL-2 promoter, the murine IL-2 promoter).

In one embodiment, an inducible system can be constructed and used in high throughput cell-based screens to identify and characterize target compounds that affect the expression and/or activity of T-bet. The inducible system can be constructed using a cell line that does not normally produce IFN-γ, for example, by using a subclone of the adherent 293T human embryonic kidney cell line that expresses the ecdysone receptor, co-transfected with an ecdysone-driven T-bet expression plasmid, and an IFN-γ promoter luciferase reporter. (Wakita et al. 2001. Biotechniques 31:414; No et al. Proceedings of the National Academy of Sciences USA 93:3346; Graham. 2002 Expert Opin. Biol. Ther. 2:525). Upon treatment with the insect hormone ecdysone, T-bet is expressed, the IFN-γ reporter is activated and luciferase activity is generated. In this system, T-bet confers on the cell line the ability to produce endogenous IFN-γ.

ii. Cell-Free Assays

In another embodiment, the indicator composition is a cell free composition. T-bet or a non-T-bet polypeptide which acts upstream or downstream of T-bet in a pathway involving T-bet expressed by recombinant methods in a host cells or culture medium can be isolated from the host cells, or cell culture medium using standard methods for purifying polypeptides, for example, by ion-exchange chromatography, gel filtration chromatography, ultrafiltration, electrophoresis, and immunoaffinity purification with antibodies specific for T-bet to produce protein that can be used in a cell free composition. Alternatively, an extract of T-bet or non-T-bet expressing cells can be prepared for use as cell-free composition.

In one embodiment, compounds that specifically modulate T-bet activity are identified based on their ability to modulate the interaction of T-bet with a target molecule to which T-bet binds. The target molecule can be a DNA molecule, e.g., a T-bet-responsive element, such as the regulatory region of a cytokine gene) or a polypeptide molecule, e.g., a kinase. Suitable assays are known in the art that allow for the detection of protein-protein interactions (e.g., immunoprecipitations, e.g., chromatin immunoprecipitations, fluorescent polarization or energy transfer, two-hybrid assays and the like) or that allow for the detection of interactions between a DNA binding protein with a target DNA sequence (e.g., electrophoretic mobility shift assays, DNAse I footprinting assays and the like). By performing such assays in the presence and absence of test compounds, these assays can be used to identify compounds that modulate (e.g., inhibit or enhance) the interaction of T-bet with a target molecule.

In one embodiment, the amount of binding of T-bet to the target molecule in the presence of the test compound is greater than the amount of binding of T-bet to the target molecule in the absence of the test compound, in which case the test compound is identified as a compound that enhances or stabilizes binding of T-bet. In another embodiment, the amount of binding of the T-bet to the target molecule in the presence of the test compound is less than the amount of binding of the T-bet to the target molecule in the absence of the test compound, in which case the test compound is identified as a compound that inhibits or destabilizes binding of T-bet.

Binding of the test compound to the T-bet polypeptide can be determined either directly or indirectly as described above. Determining the ability of the T-bet polypeptide to bind to a test compound can also be accomplished using a technology such as real-time Biomolecular Interaction Analysis (BIA) (Sjolander, S. and Urbaniczky, C. (1991) *Anal. Chem.* 63:2338-2345; Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In the methods of the invention for identifying test compounds that modulate an interaction between T-bet polypeptide and a target molecule, the full-length T-bet polypeptide may be used in the method, or, alternatively, only portions of the T-bet may be used. The degree of interaction between T-bet polypeptides and the target molecule can be determined, for example, by labeling one of the polypeptides with a detectable substance (e.g., a radiolabel), isolating the non-labeled polypeptide and quantitating the amount of detectable substance that has become associated with the non-labeled polypeptide. The assay can be used to identify test compounds that either stimulate or inhibit the interaction between the T-bet protein and a target molecule. A test compound that stimulates the interaction between the T-bet polypeptide and a target molecule is identified based upon its ability to increase the degree of interaction between the T-bet polypeptide and a target molecule as compared to the degree of interaction in the absence of the test compound. A test compound that inhibits the interaction between the T-bet polypeptide and a target molecule is identified based upon its ability to decrease the degree of interaction between the T-bet polypeptide and a target molecule as compared to the degree of interaction in the absence of the compound.

In more than one embodiment of the above assay methods of the present invention, it may be desirable to immobilize either T-bet or a T-bet target molecule, a kinase, for example, to facilitate separation of complexed from uncomplexed forms of one or both of the polypeptides, or to accommodate automation of the assay. Binding of a test compound to a T-bet polypeptide, or interaction of a T-bet polypeptide with a T-bet target molecule in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the polypeptides to be bound to a matrix. For example, glutathione-S-transferase/T-bet fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target polypeptide or T-bet polypeptide, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of T-bet binding or activity determined using standard techniques.

Other techniques for immobilizing polypeptides on matrices can also be used in the screening assays of the invention. For example, either a T-bet polypeptide or a T-bet target molecule can be immobilized utilizing conjugation of biotin and streptavidin. Biotinylated T-bet polypeptide or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with T-bet polypeptide or target molecules but which do not interfere with binding of the T-bet polypeptide to its target molecule can be derivatized to the wells of the plate, and unbound target or T-bet polypeptide is trapped in the wells by antibody conjugation. Methods for detecting such complexes, in addition to those described above for the GST-immobilized complexes, include immunodetection of complexes using antibodies reactive with the T-bet polypeptide or target molecule, as well as enzyme-linked assays which rely on detecting an enzymatic activity associated with the T-bet polypeptide or target molecule.

In yet another aspect of the invention, the T-bet polypeptide or fragments thereof can be used as "bait proteins" in a two-hybrid assay or three-hybrid assay (see, e.g. U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other polypeptides, which bind to or interact with T-bet ("T-bet-binding proteins" or "T-bet") and are involved in T-bet activity. Such T-bet-binding proteins are also likely to be involved in the propagation of signals by the T-bet polypeptides or T-bet targets as, for example, downstream elements of a T-bet-mediated signaling pathway. Alternatively, such T-bet-binding polypeptides are likely to be T-bet inhibitors.

The two-hybrid system is based on the modular nature of most transcription factors, which consist of separable DNA-binding and activation domains. Briefly, the assay utilizes two different DNA constructs. In one construct, the gene that codes for a T-bet polypeptide is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a T-bet-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the T-bet polypeptide.

In another embodiment, representational difference analysis (RDA) and microchip DNA array analysis to isolate T-bet target genes. For example, differential display or subtraction methods coupled with PCR (RDA; see e.g., Hubank, M. & Schatz, D. G. 1994. *Nuc. Acid Res.* 22, 5640-5648; Chang, Y., et al. 1994. *Science* 266, 1865; von Stein, O. D., et al. 1997. *Nuc. Acid Res.* 25, 2598; Lisitsyn, N. & Wigler, M. 1993. *Science* 259, 946) employing subtracted or unsubtracted probes or, most recently, DNA microchip array hybridization (Welford et al. 1998. *Nucl. Acids. Res.* 15:3059) can be used. In performing such assays, a variety of cells can be used, e.g., normal cells, cells engineered to express T-bet, or cells from mice lacking T-bet or overexpressing T-bet (e.g., from a transgenic non-human animal) can be used.

In yet another embodiment, proteomic approaches to describe T-bet target proteins can be performed. For example, subtractive analysis, analysis of expression patterns, identification of genotypic variations at the protein level and protein identification and detection of post-translational modifications can be performed as described in, e.g., Wang et al. (2002) *J. Chromatogr. B. Technol. Biomed. Life Sci.* 782(1-2): 291-306; Lubman et al. (2002) *J. Chromatogr. B. Technol. Biomed. Life Sci.* 782(1-2): 183-96; and Rai et al. (2002) *Arch. Pathol. Lab. Med.* 126(12):1518-26.

C. Assays Using T-Bet Deficient Cells

In another embodiment, the invention provides methods for identifying compounds that modulate a biological effect of T-bet using cells deficient in T-bet. As previously described, inhibition of T-bet activity (e.g., by disruption of the T-bet gene) in B cells results in a deficiency of IgG2a production. Thus, cells deficient in T-bet can be used identify agents that modulate a biological response regulated by T-bet by means other than modulating T-bet itself (i.e., compounds that "rescue" the T-bet deficient phenotype). Alternatively, a "conditional knock-out" system, in which the T-bet gene is rendered non-functional in a conditional manner, can be used to create T-bet deficient cells for use in screening assays. For example, a tetracycline-regulated system for conditional disruption of a gene as described in WO 94/29442 and U.S. Pat. No. 5,650,298 can be used to create cells, or T-bet deficient animals from which cells can be isolated, that can be rendered T-bet deficient in a controlled manner through modulation of the tetracycline concentration in contact with the cells. For assays relating to other biological effects of T-bet a similar conditional disruption approach can be used or, alternatively, the RAG-2 deficient blastocyst complementation system can be used to generate mice with lymphoid organs that arise from embryonic stem cells with homozygous mutations of the T-bet gene. T-bet deficient lymphoid cells (e.g., thymic, splenic and/or lymph node cells) or purified T-bet deficient B cells from such animals can be used in screening assays.

In the screening method, cells deficient in T-bet are contacted with a test compound and a biological response regulated by T-bet is monitored. Modulation of the response in T-bet deficient cells (as compared to an appropriate control such as, for example, untreated cells or cells treated with a control agent) identifies a test compound as a modulator of the T-bet regulated response.

In one embodiment, the test compound is administered directly to a non-human T-bet deficient animal, preferably a mouse (e.g., a mouse in which the T-bet gene is conditionally disrupted by means described above, or a chimeric mouse in which the lymphoid organs are deficient in T-bet as described above), to identify a test compound that modulates the in vivo responses of cells deficient in T-bet. In another embodiment, cells deficient in T-bet are isolated from the non-human T-bet deficient animal, and contacted with the test compound ex vivo to identify a test compound that modulates a response regulated by T-bet in the cells deficient in T-bet.

Cells deficient in T-bet can be obtained from a non-human animals created to be deficient in T-bet. Preferred non-human animals include monkeys, dogs, cats, mice, rats, cows, horses, goats and sheep. In preferred embodiments, the T-bet deficient animal is a mouse. Mice deficient in T-bet can be made as described in the Examples. Non-human animals deficient in a particular gene product typically are created by homologous recombination. Briefly, a vector is prepared which contains at least a portion of the T-bet gene into which a deletion, addition or substitution has been introduced to thereby alter, e.g., functionally disrupt, the endogenous T-bet gene. The T-bet gene preferably is a mouse T-bet gene. For example, a mouse T-bet gene can be isolated from a mouse genomic DNA library using the mouse T-bet cDNA as a probe. The mouse T-bet gene then can be used to construct a homologous recombination vector suitable for altering an endogenous T-bet gene in the mouse genome. In a preferred embodiment, the vector is designed such that, upon homologous recombination, the endogenous T-bet gene is functionally disrupted (i.e., no longer encodes a functional polypeptide; also referred to as a "knock out" vector). Alternatively, the vector can be designed such that, upon homologous recombination, the endogenous T-bet gene is mutated or otherwise altered but still encodes functional polypeptide (e.g., the upstream regulatory region can be altered to thereby alter the expression of the endogenous T-bet polypeptide). In the homologous recombination vector, the altered portion of the T-bet gene is flanked at its 5' and 3' ends by additional nucleic acid of the T-bet gene to allow for homologous recombination to occur between the exogenous T-bet gene carried by the vector and an endogenous T-bet gene in an embryonic stem cell. The additional flanking T-bet nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced T-bet gene has homologously recombined with the endogenous T-bet gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, retroviral transduction of donor bone marrow cells from both wild type and T-bet null mice can be performed with the DN or dominant negative constructs to reconstitute irradiated RAG recipients. This will result in the production of mice whose lymphoid cells express only a dominant negative version of T-bet. B cells from these mice can then be tested for compounds that modulate a biological response regulated by T-bet.

In one embodiment of the screening assay, compounds tested for their ability to modulate a biological response regulated by T-bet are contacted with T-bet deficient cells by administering the test compound to a non-human T-bet deficient animal in vivo and evaluating the effect of the test compound on the response in the animal. The test compound can be administered to a non-human T-bet deficient animal as a pharmaceutical composition. Such compositions typically comprise the test compound and a pharmaceutically acceptable carrier. As used herein the term "pharmaceutically acceptable carrier" is intended to include any and all solvents, dispersion media, coatings, antibacterial and antifungal compounds, isotonic and absorption delaying compounds, and the like, compatible with pharmaceutical administration. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

D. Test Compounds

A variety of test compounds can be evaluated using the screening assays described herein. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909) peptoids (Zuckermann. (1994). *J. Med. Chem.* 37:2678) oligocarbamates (Cho et al. (1993). *Science.* 261:1303- ), and hydantoins (DeWitt et al. supra). An approach for the synthesis of molecular libraries of small organic molecules with a diversity of 104-105 as been described (Carell et al. (1994). *Angew. Chem. Int. Ed. Engl.* 33:2059-; Carell et al. (1994) *Angew. Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Compound Des.* 12:145). Other exemplary methods for the synthesis of molecular libraries can be found in the art, for example in: Erb et al. (1994). *Proc. Natl. Acad. Sci. USA* 91:11422-; Horwell et al. (1996) *Immunopharmacology* 33:68-; and in Gallop et al. (1994); *J. Med. Chem.* 37:1233-.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms or T-bet molecules, e.g., dominant negative mutant forms of the molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Compound Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or phage (Scott and Smith (1990) *Science* 249:386-390; Devlin (1990)

*Science* 249:404-406; Cwirla et al. (1990) *Proc. Natl. Acad. Sci.* 87:6378-6382; Felici (1991) *J. Mol. Biol.* 222:301-310; Ladner supra.).

Compounds identified in the subject screening assays can be used in methods of modulating one or more of the biological responses regulated by T-bet. It will be understood that it may be desirable to formulate such compound(s) as pharmaceutical compositions (described supra) prior to contacting them with cells.

Once a test compound is identified that directly or indirectly modulates T-bet expression and/or activity, by one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response). Compounds of interest can also be identified using structure based drug design using techniques known in the art.

The instant invention also pertains to compounds identified in the above assays.

VII. Kits of the Invention

Another aspect of the invention pertains to kits for carrying out the screening assays of the invention. For example, a kit for carrying out a screening assay of the invention can include a T-bet-containing indicator composition, means for measuring a readout (e.g., polypeptide secretion) and instructions for using the kit to identify modulators of biological effects of T-bet. In another embodiment, a kit for carrying out a screening assay of the invention comprises T-bet deficient cells, means for measuring the readout and instructions for using the kit to identify modulators of a biological effect of T-bet.

This invention is further illustrated by the following examples, which should not be construed as limiting. The contents of all references, patents and published patent applications cited throughout this application are hereby incorporated by reference. Additionally, all nucleotide and amino acid sequences deposited in public databases referred to herein are also hereby incorporated by reference.

A nucleic acid molecule comprising a mouse T-bet cDNA cloned into the EcoRI site of the pJG4-5 vector was deposited with the American Type Culture Collection (Manassas, Va.) on Nov. 9, 1999 and assigned Deposit Number PTA-930. A nucleic acid molecule comprising a human T-bet cDNA (prepared from RNA from the human Th1 clone ROT-10) cloned into the PCR 2.1-TOPO vector was deposited with the American Type Culture Collection (Manassas, Va.) on Jan. 28, 2000 and assigned Deposit Number PTA-1339. Both deposits were made under the provisions of the Budapest Treaty.

EXAMPLES

The following Materials and Methods were used in the Examples:

Mice, Cell Lines and Reagents

T-bet$^{-/-}$ mice backcrossed more than 7 generations onto a C57BL/6 genetic background were used with wild type control C57BL/6 mice. The mouse Th1 cell clone, AE7 and mouse thymoma, EL4 cells were cultured in RPMI 1640 complete medium. Recombinant mouse cytokines were purchased from Pharmingen (San Diego, Calif.). Human recombinant IL-2, which is not recognized by mouse anti-IL-2 antibody, was obtained from Chiron (Emeryville, Calif.). All capture and biotin labeled anti-cytokine antibodies for ELISA were from Pharmingen. All mice were maintained in a pathogen-free biosafety level-3 facility at the Harvard School of Public Health and provided with water and mouse chow. The mice were negative for all pathogens as indicated by testing of sentinel animals for mouse pathogens. Handling of mice and experimental procedures were in accordance with the institutional and National Institute of Health guidelines for animal care and use.

Isolation of CD4+ Th Cells and in Vitro Differentiation

CD4+ T cells were isolated by magnetic bead purification (MACS, Miltenyi Biotec, Inc., Auburn, Calif.) from the lymph nodes of 6- to 8-week-old T-bet$^{-/-}$ and wt C57BL/6 mice and were stimulated with plate-bound anti-CD3 (2 μg/ml), and anti-CD28 (2 μg/ml) with recombinant human IL-2 (100 units/ml). For Th1 cell differentiation, anti-IL-4 (5 μg/ml) and IL-12 (2 ng/ml) were added at day 0.

Phosphorylation Mapping

Th1 cells stimulated for 72 hours were harvested and nuclear extracts were used for immunoprecipitation of T-bet proteins. Resolved T-bet proteins were stained by GelCode® blue staining solution (Pierce, Rockford, Ill.) and excised for mass spectrometry. Gel pieces were digested in-gel with trypsin and analyzed by reverse-phase LC-MS/MS in Taplin Biological Mass Spectrometry Facility (Boston, Mass.).

Retroviral Transduction and ELISA

Retroviruses producing wt and serine mutant T-bets were transduced into T-bet$^{-/-}$ Thp cells, and cells sorted for GFP on day 3 were expanded for an additional 3 days. Cells were restimulated overnight with plate-bound anti-CD3 (2 μg/ml). Whole cell extracts were prepared from the restimulated cells. Supernatants were incubated with cytokine capturing antibodies, and then incubated sequentially with biotinylated secondary antibodies, avidin-horseradish peroxidase, and phosphatase substrate (Sigma) for detection.

In Vitro Kinase Assay

Flag-tagged T-bet proteins were overexpressed in 293T cells, then immunoprecipitated using FLAG-M2 agarose. Recombinant protein kinases were incubated with T-bet proteins for 1-4 h in the presence or absence of $\gamma$-[$^{32}$P]ATP. Reactions were resolved by SDS-PAGE and phosphorylated T-bet was detected by radiography.

DNA Pull Down Assay

Whole cell extracts were prepared with HKMG buffer (10 mM Hepes, pH 7.9, 100 mM KCl, 5 mM MgCl$_2$, 10% glycerol, 0.1% NP-40 and 1 mM DTT) and incubated with biotinylated double stranded DNA and streptavidin-agarose for precipitation. Precipitates were washed with HKMG buffer three times and applied onto SDS-PAGE for Immunoblot assay.

Chromatin Immunoprecipitation (ChIP)

ChIP assays were performed according to manufacturer's instructions (Upstate Biotechnology). Cells (6×10$^7$) were cross-linked with 1.1% formaldehyde, rinsed with ice-cold PBS and resuspended in lysis buffer (10 mM Tris HCl pH 8.0, 10 mM EDTA, 0.5 mM EGTA, 0.25% Triton X-100 and protease inhibitors. Nuclei were pelleted and sonicated to yield chromatin fragments of 500 bp. The sonicated extracts were incubated with anti-RelA and anti-T-bet polyclonal Abs.

Immune complexes were washed with wash buffer containing lithium chloride. Following the last wash, antibody/protein/DNA complexes were eluted and incubated at 67° C. overnight to reverse formaldehyde crosslinks. DNA was purified using the QIAGEN PCR Purification kit (QIAGEN, Valencia, Calif.), eluted and used for PCR. The following primer set was used to amplify the IL-2 promoter; IL2p-FWD: 5'-gtttcatacagcaggcgttcattg-3'. IL2p-REV: 5'-tttcctct-tctgatgactctctgg-3'.

Example 1

Cloning of a Novel Transcription Factor, T-Bet

Since the Th1-specific region of the IL-2 promoter had been well localized (Brombacher, F., et al. 1994. Int. Immunol. 6:189-197.; Rooney, J., et al. 1995. Mol. Cell. Biol. 15, 6299-6310; Lederer, J. A., et al. 1994. J. Immunol. 152, 77-86; Durand, D., et al. 1988. Mol. Cell. Biol. 8, 1715-1724; Hoyos, B., et al. 1989. Science 244, 457-450), a yeast one hybrid approach using an IL-2 promoter-reporter and a cDNA library made from the OF6 Th1 clone was chosen to identify Th1 specific transcription factors. To validate this approach, the Th2-specific region of the IL-4 promoter was expressed in yeast and demonstrated to be transactivated by the introduction of c-Maf, but not by several other transcription factors (e.g. NFAT). C-Maf transactivation did not occur when the c-Maf response element (MARE) was mutated. Thus, the yeast one hybrid approach was utilized.

The EGY48 yeast strain was stably integrated with the IL-2 promoter/histidine construct and transformed with a cDNA library made from an anti-CD3 activated Th1 cell clone, OF6. Of $5.6 \times 10^6$ clones screened, 488 were positive in primary screening. Of the 210 clones tested during the secondary screen, 72 proved to be specific for the IL-2 promoter. To reduce the number of positive clones, the yeast clone cDNA were hybridized with cDNAs that were differentially expressed in Th1 and Th2 cell lines. These Th1-Th2 and Th2-Th1 cDNAs were made using the Clontech PCR select kit, radiolabeled and initially used in a pilot experiment to screen the 16 most strongly positive yeast clones. Of those 16 clones, 8 were positive with the Th1 (PL17) specific cDNA product probe and not with the Th2 (D10) specific cDNA product probe. Representational difference analysis (RDA; e.g., Lisitsyn. 1993. Science. 259:946; O'Neill and Sinclair. 1997. Nucleic Acids Res. 25:2681; Hubank and Schatz. 1994. Nucleic Acids Research. 22:5640; Welford et al. 1998. Nucleic Acids Research. 26:3059) with Th1-Th2 probe on 16 positive clones with control hybridization of the probe to IL-2, IFN-γ and IL-4 was performed. The specificity of the Th1 and Th2 subtracted cDNA probes is demonstrated by their detection of IL-2 and IFN-γ versus IL-4 respectively.

Restriction enzyme analyses and sequencing data revealed that all 8 of the clones were related. They fell into three groupings based on differences in the 5' and 3' untranslated regions, each of these categories representing an independent cDNA molecule. Comparing the sequence of these clones with the NCBI GenBank Sequence Database yielded homology with the T-box family of transcription factors.

Example 2

T-Bet Shares a Region of Homology with the T-Box Family Members T-Brain and Eomesodermin Brachyury or T is the founding member of a family of transcription factors that share a 200 amino acid DNA-binding domain called the T-box (reviewed in (Smith, J. 1997. Current Opinion in Genetics & Development 7, 474-480; Papaioannou, and Silver. 1998. Bioessay. 20:9; Meisler, M. H. 1997. Mammalian Genome 8, 799-800.). The Brachyury (Greek for 'short tail') mutation was first described in 1927 in heterozygous mutant animals who had a short, slightly kinked tail (Herrmann, B. G., 1990. Nature 343, 617-622). There are now eight T-box genes in the mouse not including Brachyury. These include Tbx1-6, T-brain-1 (Tbr-1) and now, T-bet, each with a distinct and usually complex expression pattern. The T-box family of transcription factors is defined by homology of family members in the DNA binding domain. The T-bet DNA binding domain (residues 138-327 of murine T-bet) is most similar to the T-box domains of murine T-brain and *Xenopus* eomesodermin and thus places T-bet in the Tbr1 subfamily of the T-box gene family. The human homologue of the murine T-bet protein is approximately 88% identical to the mouse T-bet. T-bet shares a region of homology with the T-box family members T-brain and eomesodermin. The murine T-bet DNA binding domain is most similar to the T-box domains of murine T-brain and *Xenopus* eomesodermin. There is approximately 69% amino acid identity between the three T-box regions. T-bet bears no sequence homology to other T-box family members outside of the T-box domain.

Example 3

T-Bet is Phosphorylated at Serine Residue 508 in Vivo

T-bet is expressed at high levels in AE7, a Th1 cell clone. Interestingly, there were three immunoreactive species of T-bet protein in AE7 extracts, suggesting that T-bet might be post-translationally modified. Although T-bet is tyrosine phosphorylated at residue 525 (Hwang, E. S., S et al. 2005. Science 307:430-433), it was unlikely that this single phosphorylated tyrosine could account for the multiple species detected. To test whether phosphorylation was responsible for the triple complex observed, AE7 cells were treated with calf intestinal phosphatase (CIP) in the presence or absence of phosphatase inhibitors. The upper two bands disappeared upon CIP treatment in the absence but not presence of phosphatase inhibitors, prompting the identification of the specific phosphorylation sites. Endogenous T-bet in primary Th1 cells was immunoprecipitated using anti-T-bet Ab, resolved by SDS-PAGE, and gels subsequently stained. T-bet$^{-/-}$ Th1 cells were used as a negative control. Specific T-bet protein bands were detected by Western blot and excised for mass spectrometry (MS) to analyze phosphorylated peptides. Mass spectrometry identified a specific phosphorylated peptide, which was phosphorylated at serine (S) 508 of T-bet. S508 phosphorylation was also observed by MS analysis of overexpressed T-bet in 293T cells. These results indicate that T-bet is serine phosphorylated in primary Th1 cells by a kinase that is also expressed in non-T cells.

Example 4

Serine Phosphorylation of T-Bet is Mediated by CKI and GSK-3 Kinases

To identify the specific upstream serine/threonine kinase that phosphorylates T-bet S508, the T-bet C-terminal sequence was analyzed with the scansite program (scansite.mit.edu), which predicts kinases/phosphorylation sites. The T-bet C-terminal peptide, well conserved between human and mouse, contains several serine residues; the scansite program predicted S508 as a phosphorylation site for casein kinase I (CKI). Therefore, the in vitro phosphorylation of T-bet was analyzed using a panel of recombinant protein kinases. T-bet protein was purified by immunoprecipitation from 293T cells transfected with a T-bet expression vector. Recombinant protein kinases (10 U) were incubated with precipitated T-bet and 10 µCi of γ-[$^{32}$P]ATP (6000 Ci/mM) at 37° C. for 1 h. Reaction mixtures were resolved by SDS-PAGE, and the resulting gels dried, and subjected to autoradiography. CKI, but not active ERK, phosphorylated T-bet protein in vitro. T-bet was also phosphorylated by PKA but with 1000-fold lesser efficiency than CKI. All recombinant kinases phosphorylated control substrates efficiently. To test whether CKI specifically phosphorylated S508, a serine to alanine mutant T-bet (S508A) as well as an S498A mutant as a control were constructed, then compared in vitro phosphorylation of these proteins. T-bet proteins were overexpressed in 293T cells, immunoprecipitated, comparable expression levels confirmed by Western blot and lysates then used as substrates for further studies. Although PKA-induced phosphorylation was not different among the wt, S508A and S498A T-bet proteins, CKI-mediated phosphorylation of the S508A mutant, but not the S498A control mutant, was dramatically reduced compared to wt. These data suggest that T-bet S508 is a specific phosphorylation site for CKI but that there are likely additional CKI phosphorylation sites in T-bet since residual phosphorylation of T-bet$^{S508}$ by CKI was present at very low levels.

CKI-mediated phosphorylation induces additional phosphorylation by kinases such as GSK-3. GSK-3 is a proline-directed serine/threonine kinase that recognizes prephosphorylated substrates and processively hyperphosphorylates substrates with ser/thr pentad repeats (SXXXS) (Dajani, R., et al. 2001. *Cell* 105:721-732; Cohen, P., and S. Frame. 2001. *Nat Rev Mol Cell Biol* 2:769-776). Interestingly, there are conserved GSK-3 phosphorylation sites in T-bet that are located close to S508. To determine whether T-bet could be hyperphosphorylated by GSK-3, similar amounts of T-bet proteins were pre-incubated with CKI in the presence of ATP for prephosphorylation, washed with PBS to remove excess ATP and CKI, and then reacted with GSK-3 and γ-[$^{32}$P]ATP. Hyperphosphorylation of T-bet by GSK-3 was apparent. Although GSK-3 induced wt levels of phosphorylation in the S498A mutant, GSK-3-mediated phosphorylation was markedly decreased in the S508A mutant. Furthermore, T-bet was phosphorylated by GSK-3 without prephosphorylation by CKI in vitro suggesting that T-bet was phosphorylated by endogenous CKI in 293T cells. This is consistent with our detection of T-bet$^{S508}$ phosphorylation in 293T cells by MS. Therefore, endogenous or exogenous CKI-mediated phosphorylation of T-bet$^{S508}$ precedes its subsequent phosphorylation by GSK-3 in vitro.

Example 5

T-bet$^{S508}$ is Required for its Function as a Repressor of IL-2 Gene Transcription To establish the function of serine phosphorylated T-bet in vivo, wt, S498A control mutant and S508A mutant T-bet GFP retroviruses were introduced into T-bet$^{-/-}$ primary CD4+ Th cells and stimulated. Western blot analysis confirmed that the expression level of the three transduced T-bet proteins was similar. T-bet controls the expression of multiple cytokines in Th cells. It directly activates the transcription of the IFNγ gene, indirectly represses the transcription of Th2 cytokines IL-4, IL-5 and IL-13, and represses the expression of IL-2 through unknown mechanisms. Upon TCR activation, all three T-bet retroviruses increased IFNγ production comparably and efficiently repressed Th2 cytokine production. However, the mutation of serine 508 to alanine abolished the ability of T-bet to repress the expression of both mRNA transcripts encoding IL-2 and IL-2 protein. These data demonstrate that T-bet$^{S508}$ is selectively required for its function in repressing IL-2 production.

Example 6

T-Bet Specifically Binds to a T-Box Site within the Proximal Promoter of the IL-2 Gene and Binding does not Require S508

To investigate the mechanism of such repression, it was determined whether T-bet directly bound to and transactivated or repressed IFNγ and IL-2 promoter reporters that contain T-bet binding sites. Consistent with its ability to drive endogenous IFNγ production, the T-bet S508A mutant transactivated an IFNγ promoter reporter comparably to wt and S498A control T-bet. In contrast, while T-bet and the S498A control mutant repressed IL-2 promoter activity, the S508A mutant T-bet failed to do so. This failure was not due to changes in T-bet subcellular localization; T-bet and its mutants were exclusively expressed in the nucleus. A search for T-bet binding sites within the IL-2 gene promoter yielded putative T-box binding sequences between NFAT and NF-κB binding sites in the proximal IL-2 gene promoter. Therefore, DNA-pull down assays were performed to examine the DNA binding activity of T-bet. Protein extracts expressing T-bet were incubated with biotinylated wt or mutant T-bet binding site DNA (T-box). Wt or mutant (mt) T-box sites in the IL-2 promoter as below were labeled with biotin at the 5' end and incubated with T-bet proteins. Complexes were precipitated by incubation with streptavidin-agarose beads and subjected to T-bet immunoblotting. Wt T-box site: 5'bio-attaaaactgc-cacctaagtgtgggctaacccg-3'(SEQ ID NO:5); mt T-box site: 5'bio-attaaaactgctctctaactaagggctaacccg-3' (SEQ ID NO:6). The wt T-box-containing DNA pulled down T-bet, but T-box-mutated DNA did not, demonstrating sequence-specific binding of T-bet to the IL-2 promoter. Chromatin immunoprecipitation (ChIP) assays confirmed that T-bet binds to IL-2 promoter DNA. Of note, both S508A and S498A T-bet mutants had DNA binding activity equivalent to wt T-bet. This result indicated that T-bet$^{S508}$ was not required for T-bet's ability to bind DNA, a result that is consistent with the comparable induction of IFNγ gene transcription by the S508A mutant.

Example 7

T-Bet Heterodimerizes with RelA and this Interaction Correlates with S508 Phosphorylation As alterations in DNA binding activity could not explain the failure of the S508A mutant T-bet to repress IL-2 gene expression, it was possible that T-bet controlled the activity of other factors that regulated IL-2 gene expression. It was first determined whether a physical interaction between T-bet and IL-2 activating transcription factors such as NFAT and NF-κB, occurred. NFAT is a critical activator of IL-2 gene transcription, and five distinct essential NFAT binding sites have been mapped to the IL-2 proximal promoter (Rooney, J. W., et al. 1995. *Mol Cell Biol* 15:6299-6310). A recent study demonstrated that T-bet does physically associate with NFATc2

(Mehta, D. S., et al. 2005. *Proc Natl Acad Sci USA* 102:2016-2021); however, that interaction is not dependent on T-bet$^{S508}$. NF-κB family members also participate in activation of the IL-2 gene. Coimmunoprecipitation assays of overexpressed T-bet and RelA proteins revealed that T-bet physically interacted with RelA. Notably, this interaction required T-bet$^{S508}$ as revealed by the failure of the S508A mutant T-bet to coimmunoprecipitate RelA. C-Rel, another NF-κB family member known to regulate IL-2 gene expression, also interacted with T-bet; however, this interaction did not require T-bet$^{S508}$. Endogenous interaction of T-bet and RelA was also detected in Th1 cells as described below.

Example 8

T-Bet Requires the T-Bet Binding (T-Box) Site to Repress RelA-Mediated IL-2 Gene Transcription It was determined whether the physical association of T-bet with RelA regulated IL-2 gene transactivation by RelA. Coexpression of T-bet and RelA with a 450 bp IL-2 promoter reporter revealed that T-bet interfered with IL-2 promoter transactivation by RelA. It was determined whether T-bet repression of RelA-dependent IL-2 promoter activation required T-bet binding to the T-box site and RelA binding to its target site. T-bet was not able to repress NF-κB-mediated gene activation when three copies of an NF-κB binding site-linked reporter construct was used. This result suggests that T-bet required additional sequences, likely the T-box site, to interfere with NF-κB-dependent gene activation. We tested this by utilizing 5' deletion constructs of the IL-2 promoter. T-bet overexpression inhibited the exogenous and endogenous RelA-mediated transactivation of the 2 kb and 250 bp IL-2 promoter constructs that contain both T-box and NF-κB sites. However, activation of the 210 bp IL-2 promoter construct where the T-box site has been deleted was not repressed by T-bet expression. It was also determined whether RelA might similarly inhibit T-bet activity. Co-expression of T-bet and RelA with a T-box site-linked reporter construct or with a 450 bp IFNγ promoter-reporter in EL4 cells revealed no effect of RelA on T-bet-induced IFNγ promoter activity. It was concluded that T-bet requires the T-box binding site to repress NF-κB-mediated gene transcription. Further, the T-bet/RelA heterodimer functions only to regulate RelA and not T-bet-mediated gene activation, at least for the genes interrogated here.

Example 9

T-Bet Regulates NF-κB DNA Binding Activity to the IL-2 Gene: RelA DNA Binding Activity is Increased in T-Bet$^{-/-}$ Th1 Cells It was determined whether the physical interaction of T-bet with RelA and its repression of RelA-mediated IL-2 gene activation might affect the binding of RelA to DNA. Indeed, the repressor function of T-bet for IL-21 gene transcription was secondary to an interaction of T-bet with NFATc2 that interfered with its binding to DNA (Mehta, D. S., et al. 2005. *Proc Natl Acad Sci USA* 102:2016-2021). Although NFAT binding activity to the IL-2 promoter was not affected by concomitant T-bet expression, it was found that the DNA binding activity of RelA to the IL-2 promoter was markedly reduced in the presence of T-bet. Of note, in contrast to wt T-bet, S508A mutant T-bet did not inhibit RelA DNA binding to the IL-2 promoter. Comparable expression levels and DNA binding activities of T-bet proteins were confirmed by Western blot analysis. Thus, serine 508 of T-bet is not required for its own interaction with DNA. Instead, serine 508 is required for T-bet interference with the binding of RelA to the IL-2 promoter.

To establish the physiological relevance of this phenomenon, RelA DNA binding activity was measured over time in T-bet$^{-/-}$ as compared to wt Th1 cells. There was no obvious difference in protein expression levels of RelA between wt and T-bet$^{-/-}$ Th1 cells and RelA was continuously expressed at all stages of Th1 cell differentiation. However, the DNA binding activity of RelA was substantially increased in T-bet$^{-/-}$ Th1 cells by day 2 after TCR stimulation. In contrast, c-Rel was expressed in early developing Th1 cells and decreased after day 3 in Th1 cell differentiation. Similarly, c-Rel DNA binding activity continued to increase up to day 3, but was no longer detected after day 3 in developing Th1 cells, although two species of c-Rel with different DNA binding activities were present. The NF-κB p50 subunit was continuously expressed over time in developing Th1 cells, similar to RelA. Increased DNA binding of RelA could not be attributed to increased amounts of nuclear RelA protein as Western blot analysis of nuclear extracts prepared from wt and T-bet$^{-/-}$ Th1 cells revealed equal expression of RelA. In order to investigate the physiological relationship between RelA and T-bet, experiments to detect an endogenous interaction of T-bet and RelA in developing Th1 cells were performed. Preliminary experiments done at d6 of Th1 differentiation revealed an association of endogenous T-bet and RelA. A time course analysis of this association revealed that it did not occur until day 3 and then persisted through day 6, correlating nicely with the decreased IL-2 expression observed in late developing Th1 cells. Taken together, these results are consistent with the notion that the interaction of RelA and T-bet downregulates IL-2 production in late but not early Th1 cell differentiation.

Example 10

RelA DNA Binding Activity Correlates with Endogenous IL-2 mRNA Transcripts and Protein The relationship between T-bet-controlled RelA DNA-binding activity and IL-2 gene transcription during Th1 differentiation was next investigated. Levels of IL-2 protein and transcripts during Th1 cell differentiation of wt and T-bet$^{-/-}$ Th cells were compared. Of note, there was no difference in levels of IL-2 produced by wt and T-bet$^{-/-}$ Th cells at day 2. This is consistent with a report that reconstitution of mice with fetal liver from RelA$^{-/-}$ embryos revealed no defect in IL-2 production at 18 hrs and strongly suggests a primary role for c-Rel and not RelA, at early time points (Doi, T. S., et al. 1997. *J Exp Med* 185:953-961). However, by day 3, there was significantly more IL-2 secreted by T-bet$^{-/-}$ as compared to wt Th1 cells. As IL-2 protein was undetectable at later time points by ELISA, likely due increased consumption of it by activated Th cells, the kinetics of IL-2 mRNA expression during Th1 cell differentiation were measured. IL-2 transcripts were induced by TCR stimulation, but gradually decreased in developing wt Th1 cells consistent with a repression of IL-2 gene expression. In contrast, IL-2 transcripts persisted in T-bet$^{-/-}$ Th1 cells, consistent with a repressor role of T-bet at that stage of differentiation. Th1 polarization was confirmed by measuring IFNγ protein which increased in wt Th1 cells, peaked at day 3 and gradually decreased while IFNγ transcripts continuously increased over time. As expected, protein and mRNA levels of IFNγ were almost completely absent in T-bet$^{-/-}$ Th1 cells (Szabo, S. J., et al.

2002. *Science* 295:338-342) (Specific primers used were: IFNγ-FWD 5'-agcaacagcaaggcgaaaa-3'(SEQ ID NO:7), IFNγ-REV, 5'-ctggacctgtgggttgttga-3'(SEQ ID NO:8)). Further, substantially increased levels of Transcripts encoding IL-2 as well as increased IL-2 protein in re-stimulated T-bet$^{-/-}$ Th1 cells as compared to wt Th1 cells were observed. This is consistent with the repression of IL-2 mRNA and protein that was observed with T-bet overexpression.

To directly test whether T-bet expression controlled binding of RelA to IL-2 promoter DNA, chromatin immunoprecipitation (ChIP) assays were used. DNA/protein complexes in late stage developing wt and T-bet$^{-/-}$ Th1 cells were immunoprecipitated with anti-RelA polyclonal antibody and detected by PCR and real-time PCR. Increased IL-2 promoter binding of RelA in T-bet$^{-/-}$ Th1 cells was observed in PCR reactions. Real-time PCR quantitatively measured IL-2 promoter binding of RelA compared to input DNA and revealed a 4.5-fold increase in T-bet$^{-/-}$ Th1 cells. Therefore, RelA DNA binding activity is increased in Th1 cells lacking T-bet and correlates with an increase in endogenous IL-2 mRNA transcripts and protein. Taken together these studies provide strong evidence that the interaction of T-bet with RelA interferes with the binding of RelA to IL-2 promoter DNA and hence the coactivation of IL-2 gene expression by RelA. Further, this process depends upon serine 508 of T-bet and is closely correlated with phosphorylation of that residue.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying a compound which modulates interleukin 2 (IL-2) production, comprising contacting in the presence of the compound, T-bet polypeptide and a casein kinase I (CKI) polypeptide under conditions which allow interaction of the kinase polypeptide with the T-bet polypeptide; and detecting the interaction of the T-bet polypeptide and the kinase polypeptide, wherein the ability of the compound to increase IL-2 production is indicated by a decrease in the interaction as compared to the amount of interaction in the absence of the compound, and the ability of the compound to decrease IL-2 production is indicated by a increase in the interaction as compared to the amount of interaction in the absence of the compound.

2. The method of claim 1, wherein the interaction of the T-bet polypeptide and the kinase polypeptide is determined by measuring the formation of a complex between the T-bet polypeptide and the kinase polypeptide.

3. The method of claim 1, wherein the interaction of the T-bet polypeptide and the kinase polypeptide is determined by measuring the phosphorylation of the T-bet polypeptide.

4. The method of claim 3, wherein the phosphorylation of T-bet polypeptide is determined by measuring the phosphorylation of the serine residue at amino acid position 508 (S508) of T-bet.

5. The method of claim 1, wherein the production of IL-2 is measured by determining IL-2 mRNA levels.

6. The method of claim 1, wherein the production of IL-2 is measured by determining IL-2 protein levels.

7. The method of claim 1, wherein the compound increases IL-2 production.

8. The method of claim 1, wherein the compound decreases IL-2 production.

9. The method of claim 1 which is conducted using a cell-free system.

10. The method of claim 1 which is conducted using a cell-based system.

11. The method of claim 10, wherein the cell has been engineered to express the T-bet polypeptide by introducing into the cell an expression vector encoding the T-bet polypeptide.

* * * * *

UNITED STATES PATENT AND TRADEMARK OFFICE
CERTIFICATE OF CORRECTION

PATENT NO. : 7,592,147 B2  
APPLICATION NO. : 11/593811  
DATED : September 22, 2009  
INVENTOR(S) : Laurie H. Glimcher et al.

Page 1 of 1

It is certified that error appears in the above-identified patent and that said Letters Patent is hereby corrected as shown below:

In the Specification

At Column 1, Line number 14, please delete the paragraph labeled "GOVERNMENT FUNDING" and replace it with the following paragraph:

--This invention was made with government support under AG037833, AI036535, AI039646, AR062227, AI007290, CA048126, and AI056296 awarded by the National Institutes of Health. The government has certain rights in the invention.--

Signed and Sealed this
Eleventh Day of August, 2020

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 1608
<212> TYPE: DNA
<213> ORGANISM: Homo sapiens
<220> FEATURE:
<221> NAME/KEY: CDS
<222> LOCATION: (1)..(1605)

<400> SEQUENCE: 1 atg ggc atc gtg gag ccg ggt tgc gga gac atg ctg acg ggc acc gag      48
Met Gly Ile Val Glu Pro Gly Cys Gly Asp Met Leu Thr Gly Thr Glu
  1               5                  10                  15 ccg atg ccg ggg agc gac gag ggc cgg gcg cct ggc gcc gac ccg cag      96
Pro Met Pro Gly Ser Asp Glu Gly Arg Ala Pro Gly Ala Asp Pro Gln
             20                  25                  30 cac cgc tac ttc tac ccg gag ccg ggc gcg cag gac gcg gac gag cgt     144
His Arg Tyr Phe Tyr Pro Glu Pro Gly Ala Gln Asp Ala Asp Glu Arg
         35                  40                  45 cgc ggg ggc ggc agc ctg ggg tct ccc tac ccg ggg ggc gcc ttg gtg     192
Arg Gly Gly Gly Ser Leu Gly Ser Pro Tyr Pro Gly Gly Ala Leu Val
     50                  55                  60 ccc gcc ccg ccg agc cgc ttc ctt gga gcc tac gcc tac ccg ccg cga     240
Pro Ala Pro Pro Ser Arg Phe Leu Gly Ala Tyr Ala Tyr Pro Pro Arg
 65                  70                  75                  80 ccc cag gcg gcc ggc ttc ccc ggc gcg ggc gag tcc ttc ccg ccg ccc     288
Pro Gln Ala Ala Gly Phe Pro Gly Ala Gly Glu Ser Phe Pro Pro Pro
                 85                  90                  95 gcg gac gcc gag ggc tac cag ccg ggc gag ggc tac gcc gcc ccg gac     336
Ala Asp Ala Glu Gly Tyr Gln Pro Gly Glu Gly Tyr Ala Ala Pro Asp
            100                 105                 110 ccg cgc gcc ggg ctc tac ccg ggg ccg cgt gag gac tac gcg cta ccc     384
Pro Arg Ala Gly Leu Tyr Pro Gly Pro Arg Glu Asp Tyr Ala Leu Pro
        115                 120                 125 gcg gga ctg gag gtg tcg ggg aaa ctg agg gtc gcg ctc aac aac cac     432
Ala Gly Leu Glu Val Ser Gly Lys Leu Arg Val Ala Leu Asn Asn His
    130                 135                 140 ctg ttg tgg tcc aag ttt aat cag cac cag aca gag atg atc atc acc     480
Leu Leu Trp Ser Lys Phe Asn Gln His Gln Thr Glu Met Ile Ile Thr
145                 150                 155                 160 aag cag gga cgg cgg atg ttc cca ttc ctg tca ttt act gtg gcc ggg     528
Lys Gln Gly Arg Arg Met Phe Pro Phe Leu Ser Phe Thr Val Ala Gly
```

-continued

|  | 165 |  |  |  | 170 |  |  |  | 175 |  |  |  |  |
|---|---|---|---|---|---|---|---|---|---|---|---|---|---|
| ctg | gag | ccc | acc | agc | cac | tac | agg | atg | ttt | gtg | gac | gtg | gtc ttg gtg | 576 |
| Leu | Glu | Pro | Thr | Ser | His | Tyr | Arg | Met | Phe | Val | Asp | Val | Val Leu Val | |
|  |  |  | 180 |  |  |  |  | 185 |  |  |  | 190 | | |

```
ctg gag ccc acc agc cac tac agg atg ttt gtg gac gtg gtc ttg gtg      576
Leu Glu Pro Thr Ser His Tyr Arg Met Phe Val Asp Val Val Leu Val
            180                 185                 190 gac cag cac cac tgg cgg tac cag agc ggc aag tgg gtg cag tgt gga      624
Asp Gln His His Trp Arg Tyr Gln Ser Gly Lys Trp Val Gln Cys Gly
        195                 200                 205 aag gcc gag ggc agc atg cca gga aac cgc ctg tac gtc cac ccg gac      672
Lys Ala Glu Gly Ser Met Pro Gly Asn Arg Leu Tyr Val His Pro Asp
    210                 215                 220 tcc ccc aac aca gga gcg cac tgg atg cgc cag gaa gtt tca ttt ggg      720
Ser Pro Asn Thr Gly Ala His Trp Met Arg Gln Glu Val Ser Phe Gly
225                 230                 235                 240 aaa cta aag ctc aca aac aac aag ggg gcg tcc aac aat gtg acc cag      768
Lys Leu Lys Leu Thr Asn Asn Lys Gly Ala Ser Asn Asn Val Thr Gln
            245                 250                 255 atg att gtg ctc cag tcc ctc cat aag tac cag ccc cgg ctg cat atc      816
Met Ile Val Leu Gln Ser Leu His Lys Tyr Gln Pro Arg Leu His Ile
        260                 265                 270 gtt gag gtg aac gac gga gag cca gag gca gcc tgc aac gct tcc aac      864
Val Glu Val Asn Asp Gly Glu Pro Glu Ala Ala Cys Asn Ala Ser Asn
    275                 280                 285 acg cat atc ttt act ttc caa gaa acc cag ttc att gcc gtg act gcc      912
Thr His Ile Phe Thr Phe Gln Glu Thr Gln Phe Ile Ala Val Thr Ala
290                 295                 300 tac cag aat gcc gag att act cag ctg aaa att gat aat aac ccc ttt      960
Tyr Gln Asn Ala Glu Ile Thr Gln Leu Lys Ile Asp Asn Asn Pro Phe
305                 310                 315                 320 gcc aaa gga ttc cgg gag aac ttt gag tcc atg tac aca tct gtt gac     1008
Ala Lys Gly Phe Arg Glu Asn Phe Glu Ser Met Tyr Thr Ser Val Asp
            325                 330                 335 acc agc atc ccc tcc ccg cct gga ccc aac tgt caa ttc ctt ggg gga     1056
Thr Ser Ile Pro Ser Pro Pro Gly Pro Asn Cys Gln Phe Leu Gly Gly
        340                 345                 350 gat cac tac tct cct ctc cta ccc aac cag tat cct gtt ccc agc cgc     1104
Asp His Tyr Ser Pro Leu Leu Pro Asn Gln Tyr Pro Val Pro Ser Arg
    355                 360                 365 ttc tac ccc gac ctt cct ggc cag gcg aag gat gtg gtt ccc cag gct     1152
Phe Tyr Pro Asp Leu Pro Gly Gln Ala Lys Asp Val Val Pro Gln Ala
370                 375                 380 tac tgg ctg ggg gcc ccc cgg gac cac agc tat gag gct gag ttt cga     1200
Tyr Trp Leu Gly Ala Pro Arg Asp His Ser Tyr Glu Ala Glu Phe Arg
385                 390                 395                 400 gca gtc agc atg aag cct gca ttc ttg ccc tct gcc cct ggg ccc acc     1248
Ala Val Ser Met Lys Pro Ala Phe Leu Pro Ser Ala Pro Gly Pro Thr
            405                 410                 415 atg tcc tac tac cga ggc cag gag gtc ctg gca cct gga gct ggc tgg     1296
Met Ser Tyr Tyr Arg Gly Gln Glu Val Leu Ala Pro Gly Ala Gly Trp
        420                 425                 430 cct gtg gca ccc cag tac cct ccc aag atg ggc ccg gcc agc tgg ttc     1344
Pro Val Ala Pro Gln Tyr Pro Pro Lys Met Gly Pro Ala Ser Trp Phe
    435                 440                 445 cgc cct atg cgg act ctg ccc atg gaa ccc ggc cct gga ggc tca gag     1392
Arg Pro Met Arg Thr Leu Pro Met Glu Pro Gly Pro Gly Gly Ser Glu
450                 455                 460 gga cgg gga cca gag gac cag ggt ccc ccc ttg gtg tgg act gag att     1440
Gly Arg Gly Pro Glu Asp Gln Gly Pro Pro Leu Val Trp Thr Glu Ile
465                 470                 475                 480 gcc ccc atc cgg ccg gaa tcc agt gat tca gga ctg ggc gaa gga gac     1488
Ala Pro Ile Arg Pro Glu Ser Ser Asp Ser Gly Leu Gly Glu Gly Asp
```

```
Ala Pro Ile Arg Pro Glu Ser Ser Asp Ser Gly Leu Gly Glu Gly Asp
                485                 490                 495 tct aag agg agg cgc gtg tcc ccc tat cct tcc agt ggt gac agc tcc      1536
Ser Lys Arg Arg Arg Val Ser Pro Tyr Pro Ser Ser Gly Asp Ser Ser
        500                 505                 510 tcc cct gct ggg gcc cct tct cct ttt gat aag gaa gct gaa gga cag      1584
Ser Pro Ala Gly Ala Pro Ser Pro Phe Asp Lys Glu Ala Glu Gly Gln
            515                 520                 525 ttt tat aac tat ttt ccc aac tga                                      1608
Phe Tyr Asn Tyr Phe Pro Asn
        530                 535

<210> SEQ ID NO 2
<211> LENGTH: 535
<212> TYPE: PRT
<213> ORGANISM: Homo sapiens

<400> SEQUENCE: 2

Met Gly Ile Val Glu Pro Gly Cys Gly Asp Met Leu Thr Gly Thr Glu
 1               5                  10                  15

Pro Met Pro Gly Ser Asp Glu Gly Arg Ala Pro Gly Ala Asp Pro Gln
            20                  25                  30

His Arg Tyr Phe Tyr Pro Glu Pro Gly Ala Gln Asp Ala Asp Glu Arg
        35                  40                  45

Arg Gly Gly Gly Ser Leu Gly Ser Pro Tyr Pro Gly Gly Ala Leu Val
    50                  55                  60

Pro Ala Pro Pro Ser Arg Phe Leu Gly Ala Tyr Ala Tyr Pro Pro Arg
65                  70                  75                  80

Pro Gln Ala Ala Gly Phe Pro Gly Ala Gly Glu Ser Phe Pro Pro Pro
                85                  90                  95

Ala Asp Ala Glu Gly Tyr Gln Pro Gly Glu Gly Tyr Ala Ala Pro Asp
            100                 105                 110

Pro Arg Ala Gly Leu Tyr Pro Gly Pro Arg Glu Asp Tyr Ala Leu Pro
        115                 120                 125

Ala Gly Leu Glu Val Ser Gly Lys Leu Arg Val Ala Leu Asn Asn His
    130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
            180                 185                 190

Asp Gln His His Trp Arg Tyr Gln Ser Gly Lys Trp Val Gln Cys Gly
        195                 200                 205

Lys Ala Glu Gly Ser Met Pro Gly Asn Arg Leu Tyr Val His Pro Asp
    210                 215                 220

Ser Pro Asn Thr Gly Ala His Trp Met Arg Gln Glu Val Ser Phe Gly
225                 230                 235                 240

Lys Leu Lys Leu Thr Asn Asn Lys Gly Ala Ser Asn Asn Val Thr Gln
                245                 250                 255

Met Ile Val Leu Gln Ser Leu His Lys Tyr Gln Pro Arg Leu His Ile
            260                 265                 270

Val Glu Val Asn Asp Gly Glu Pro Glu Ala Ala Cys Asn Ala Ser Asn
        275                 280                 285

Thr His Ile Phe Thr Phe Gln Glu Thr Gln Phe Ile Ala Val Thr Ala
    290                 295                 300
```

```
Tyr Gln Asn Ala Glu Ile Thr Gln Leu Lys Ile Asp Asn Asn Pro Phe
305                 310                 315                 320

Ala Lys Gly Phe Arg Glu Asn Phe Glu Ser Met Tyr Thr Ser Val Asp
            325                 330                 335

Thr Ser Ile Pro Ser Pro Pro Gly Pro Asn Cys Gln Phe Leu Gly Gly
            340                 345                 350

Asp His Tyr Ser Pro Leu Leu Pro Asn Gln Tyr Pro Val Pro Ser Arg
            355                 360                 365

Phe Tyr Pro Asp Leu Pro Gly Gln Ala Lys Asp Val Val Pro Gln Ala
    370                 375                 380

Tyr Trp Leu Gly Ala Pro Arg Asp His Ser Tyr Glu Ala Glu Phe Arg
385                 390                 395                 400

Ala Val Ser Met Lys Pro Ala Phe Leu Pro Ser Ala Pro Gly Pro Thr
            405                 410                 415

Met Ser Tyr Tyr Arg Gly Gln Glu Val Leu Ala Pro Gly Ala Gly Trp
            420                 425                 430

Pro Val Ala Pro Gln Tyr Pro Pro Lys Met Gly Pro Ala Ser Trp Phe
    435                 440                 445

Arg Pro Met Arg Thr Leu Pro Met Glu Pro Gly Pro Gly Gly Ser Glu
450                 455                 460

Gly Arg Gly Pro Glu Asp Gln Gly Pro Pro Leu Val Trp Thr Glu Ile
465                 470                 475                 480

Ala Pro Ile Arg Pro Glu Ser Ser Asp Ser Gly Leu Gly Glu Gly Asp
            485                 490                 495

Ser Lys Arg Arg Arg Val Ser Pro Tyr Pro Ser Ser Gly Asp Ser Ser
            500                 505                 510

Ser Pro Ala Gly Ala Pro Ser Pro Phe Asp Lys Glu Ala Glu Gly Gln
    515                 520                 525

Phe Tyr Asn Tyr Phe Pro Asn
    530                 535

<210> SEQ ID NO 3
<211> LENGTH: 1593
<212> TYPE: DNA
<213> ORGANISM: Mus musculus
<220> FEATURE:
<221> NAME/KEY: CDS
<222> LOCATION: (1)..(1590)

<400> SEQUENCE: 3 atg ggc atc gtg gag ccg ggc tgc gga gac atg ctg acc ggc acc gag       48
Met Gly Ile Val Glu Pro Gly Cys Gly Asp Met Leu Thr Gly Thr Glu
1               5                   10                  15 ccg atg ccg agt gac gag ggc cgg ggg ccc gga gcg gac caa cag cat       96
Pro Met Pro Ser Asp Glu Gly Arg Gly Pro Gly Ala Asp Gln Gln His
            20                  25                  30 cgt ttc ttc tat ccc gag ccg ggc gca cag gac ccg acc gat cgc cgc      144
Arg Phe Phe Tyr Pro Glu Pro Gly Ala Gln Asp Pro Thr Asp Arg Arg
        35                  40                  45 gca ggt agc agc ctg ggg acg ccc tac tct ggg ggc gcc ctg gtg cct      192
Ala Gly Ser Ser Leu Gly Thr Pro Tyr Ser Gly Gly Ala Leu Val Pro
    50                  55                  60 gcc gcg ccg ggt cgc ttc ctt gga tcc ttc gcc tac ccg ccc cgg gct      240
Ala Ala Pro Gly Arg Phe Leu Gly Ser Phe Ala Tyr Pro Pro Arg Ala
65                  70                  75                  80 cag gtg gct ggc ttt ccc ggg cct ggc gag ttc ttc ccg ccg ccc gcg      288
Gln Val Ala Gly Phe Pro Gly Pro Gly Glu Phe Phe Pro Pro Pro Ala
```

-continued

```
                       85                    90                   95
ggt gcg gag ggc tac ccg ccc gtg gat ggc tac cct gcc cct gac ccg       336
Gly Ala Glu Gly Tyr Pro Pro Val Asp Gly Tyr Pro Ala Pro Asp Pro
                      100                   105                  110 cgc gcg ggg ctc tac cca ggg ccg cgc gag gac tac gca ttg ccc gcg       384
Arg Ala Gly Leu Tyr Pro Gly Pro Arg Glu Asp Tyr Ala Leu Pro Ala
                      115                   120                  125 ggg ttg gag gtg tct ggg aag ctg aga gtc gcg ctc agc aac cac ctg       432
Gly Leu Glu Val Ser Gly Lys Leu Arg Val Ala Leu Ser Asn His Leu
            130                   135                   140 ttg tgg tcc aag ttc aac cag cac cag aca gag atg atc atc act aag       480
Leu Trp Ser Lys Phe Asn Gln His Gln Thr Glu Met Ile Ile Thr Lys
145                   150                   155                  160 caa gga cgg cga atg ttc cca ttc ctg tcc ttc acc gtg gcc ggg ctg       528
Gln Gly Arg Arg Met Phe Pro Phe Leu Ser Phe Thr Val Ala Gly Leu
                      165                   170                  175 gag ccc aca agc cat tac agg atg ttt gtg gat gtg gtc ttg gtg gac       576
Glu Pro Thr Ser His Tyr Arg Met Phe Val Asp Val Val Leu Val Asp
                      180                   185                  190 cag cac cac tgg cgg tac cag agc ggc aag tgg gtg cag tgt gga aag       624
Gln His His Trp Arg Tyr Gln Ser Gly Lys Trp Val Gln Cys Gly Lys
                      195                   200                  205 gca gaa ggc agc atg cca ggg aac cgc tta tat gtc cac cca gac tcc       672
Ala Glu Gly Ser Met Pro Gly Asn Arg Leu Tyr Val His Pro Asp Ser
            210                   215                   220 ccc aac acc gga gcc cac tgg atg cgc cag gaa gtt tca ttt ggg aag       720
Pro Asn Thr Gly Ala His Trp Met Arg Gln Glu Val Ser Phe Gly Lys
225                   230                   235                  240 cta aag ctc acc aac aac aag ggg gct tcc aac aat gtg acc cag atg       768
Leu Lys Leu Thr Asn Asn Lys Gly Ala Ser Asn Asn Val Thr Gln Met
                      245                   250                  255 atc gtc ctg cag tct ctc cac aag tac cag ccc cgg ctg cac atc gtg       816
Ile Val Leu Gln Ser Leu His Lys Tyr Gln Pro Arg Leu His Ile Val
                      260                   265                  270 gag gtg aat gat gga gag cca gag gct gcc tgc agt gct tct aac aca       864
Glu Val Asn Asp Gly Glu Pro Glu Ala Ala Cys Ser Ala Ser Asn Thr
            275                   280                   285 cac gtc ttt act ttc caa gag acc cag ttc att gca gtg act gcc tac       912
His Val Phe Thr Phe Gln Glu Thr Gln Phe Ile Ala Val Thr Ala Tyr
            290                   295                   300 cag aac gca gag atc act cag ctg aaa atc gac aac aac ccc ttt gcc       960
Gln Asn Ala Glu Ile Thr Gln Leu Lys Ile Asp Asn Asn Pro Phe Ala
305                   310                   315                  320 aaa gga ttc cgg gag aac ttt gag tcc atg tac gca tct gtt gat acg      1008
Lys Gly Phe Arg Glu Asn Phe Glu Ser Met Tyr Ala Ser Val Asp Thr
                      325                   330                  335 agt gtc ccc tcg cca cct gga ccc aac tgt caa ctg ctt ggg gga gac      1056
Ser Val Pro Ser Pro Pro Gly Pro Asn Cys Gln Leu Leu Gly Gly Asp
                      340                   345                  350 ccc ttc tca cct ctt cta tcc aac cag tat cct gtt ccc agc cgt ttc      1104
Pro Phe Ser Pro Leu Leu Ser Asn Gln Tyr Pro Val Pro Ser Arg Phe
            355                   360                   365 tac ccc gac ctt cca ggc cag ccc aag gat atg atc tca cag cct tac      1152
Tyr Pro Asp Leu Pro Gly Gln Pro Lys Asp Met Ile Ser Gln Pro Tyr
            370                   375                   380 tgg ctg ggg aca cct cgg gaa cac agt tat gaa gcg gag ttc cga gct      1200
Trp Leu Gly Thr Pro Arg Glu His Ser Tyr Glu Ala Glu Phe Arg Ala
385                   390                   395                  400 gtg agc atg aag ccc aca ctc cta ccc tct gcc ccg ggg ccc act gtg      1248
Val Ser Met Lys Pro Thr Leu Leu Pro Ser Ala Pro Gly Pro Thr Val
```

```
Val Ser Met Lys Pro Thr Leu Leu Pro Ser Ala Pro Gly Pro Thr Val
            405                 410                 415 ccc tac tac cgg ggc caa gac gtc ctg gcg cct gga gct ggt tgg ccc    1296
Pro Tyr Tyr Arg Gly Gln Asp Val Leu Ala Pro Gly Ala Gly Trp Pro
                420                 425                 430 gtg gcc cct caa tac ccg ccc aag atg agc cca gct ggc tgg ttc cgg    1344
Val Ala Pro Gln Tyr Pro Pro Lys Met Ser Pro Ala Gly Trp Phe Arg
            435                 440                 445 ccc atg cga act ctg ccc atg gac ccg ggc ctg gga tcc tca gag gaa    1392
Pro Met Arg Thr Leu Pro Met Asp Pro Gly Leu Gly Ser Ser Glu Glu
        450                 455                 460 cag ggc tcc tcc ccc tcg ctg tgg cct gag gtc acc tcc ctc cag ccg    1440
Gln Gly Ser Ser Pro Ser Leu Trp Pro Glu Val Thr Ser Leu Gln Pro
465                 470                 475                 480 gag ccc agc gac tca gga cta ggc gaa gga gac act aag agg agg agg    1488
Glu Pro Ser Asp Ser Gly Leu Gly Glu Gly Asp Thr Lys Arg Arg Arg
                485                 490                 495 ata tcc ccc tat cct tcc agt ggc gac agc tcc tct ccc gct ggg gcc    1536
Ile Ser Pro Tyr Pro Ser Ser Gly Asp Ser Ser Ser Pro Ala Gly Ala
            500                 505                 510 cct tct cct ttt gat aag gaa acc gaa ggc cag ttt tat aat tat ttt    1584
Pro Ser Pro Phe Asp Lys Glu Thr Glu Gly Gln Phe Tyr Asn Tyr Phe
        515                 520                 525 ccc aac tga                                                        1593
Pro Asn
    530

<210> SEQ ID NO 4
<211> LENGTH: 530
<212> TYPE: PRT
<213> ORGANISM: Mus musculus

<400> SEQUENCE: 4

Met Gly Ile Val Glu Pro Gly Cys Gly Asp Met Leu Thr Gly Thr Glu
  1               5                  10                  15

Pro Met Pro Ser Asp Glu Gly Arg Gly Pro Gly Ala Asp Gln Gln His
                20                  25                  30

Arg Phe Phe Tyr Pro Glu Pro Gly Ala Gln Asp Pro Thr Asp Arg Arg
            35                  40                  45

Ala Gly Ser Ser Leu Gly Thr Pro Tyr Ser Gly Gly Ala Leu Val Pro
        50                  55                  60

Ala Ala Pro Gly Arg Phe Leu Gly Ser Phe Ala Tyr Pro Pro Arg Ala
65                  70                  75                  80

Gln Val Ala Gly Phe Pro Gly Pro Gly Glu Phe Phe Pro Pro Pro Ala
                85                  90                  95

Gly Ala Glu Gly Tyr Pro Pro Val Asp Gly Tyr Pro Ala Pro Asp Pro
            100                 105                 110

Arg Ala Gly Leu Tyr Pro Gly Pro Arg Glu Asp Tyr Ala Leu Pro Ala
        115                 120                 125

Gly Leu Glu Val Ser Gly Lys Leu Arg Val Ala Leu Ser Asn His Leu
    130                 135                 140

Leu Trp Ser Lys Phe Asn Gln His Gln Thr Glu Met Ile Ile Thr Lys
145                 150                 155                 160

Gln Gly Arg Arg Met Phe Pro Phe Leu Ser Phe Thr Val Ala Gly Leu
                165                 170                 175

Glu Pro Thr Ser His Tyr Arg Met Phe Val Asp Val Val Leu Val Asp
            180                 185                 190
```

-continued

```
Gln His His Trp Arg Tyr Gln Ser Gly Lys Trp Val Gln Cys Gly Lys
    195                 200                 205
Ala Glu Gly Ser Met Pro Gly Asn Arg Leu Tyr Val His Pro Asp Ser
    210                 215                 220
Pro Asn Thr Gly Ala His Trp Met Arg Gln Glu Val Ser Phe Gly Lys
225                 230                 235                 240
Leu Lys Leu Thr Asn Asn Lys Gly Ala Ser Asn Asn Val Thr Gln Met
                245                 250                 255
Ile Val Leu Gln Ser Leu His Lys Tyr Gln Pro Arg Leu His Ile Val
                260                 265                 270
Glu Val Asn Asp Gly Glu Pro Glu Ala Ala Cys Ser Ala Ser Asn Thr
                275                 280                 285
His Val Phe Thr Phe Gln Glu Thr Gln Phe Ile Ala Val Thr Ala Tyr
                290                 295                 300
Gln Asn Ala Glu Ile Thr Gln Leu Lys Ile Asp Asn Asn Pro Phe Ala
305                 310                 315                 320
Lys Gly Phe Arg Glu Asn Phe Glu Ser Met Tyr Ala Ser Val Asp Thr
                325                 330                 335
Ser Val Pro Ser Pro Pro Gly Pro Asn Cys Gln Leu Leu Gly Gly Asp
                340                 345                 350
Pro Phe Ser Pro Leu Leu Ser Asn Gln Tyr Pro Val Pro Ser Arg Phe
                355                 360                 365
Tyr Pro Asp Leu Pro Gly Gln Pro Lys Asp Met Ile Ser Gln Pro Tyr
    370                 375                 380
Trp Leu Gly Thr Pro Arg Glu His Ser Tyr Glu Ala Glu Phe Arg Ala
385                 390                 395                 400
Val Ser Met Lys Pro Thr Leu Leu Pro Ser Ala Pro Gly Pro Thr Val
                405                 410                 415
Pro Tyr Tyr Arg Gly Gln Asp Val Leu Ala Pro Gly Ala Gly Trp Pro
                420                 425                 430
Val Ala Pro Gln Tyr Pro Pro Lys Met Ser Pro Ala Gly Trp Phe Arg
    435                 440                 445
Pro Met Arg Thr Leu Pro Met Asp Pro Gly Leu Gly Ser Ser Glu Glu
    450                 455                 460
Gln Gly Ser Ser Pro Ser Leu Trp Pro Glu Val Thr Ser Leu Gln Pro
465                 470                 475                 480
Glu Pro Ser Asp Ser Gly Leu Gly Glu Gly Asp Thr Lys Arg Arg Arg
                485                 490                 495
Ile Ser Pro Tyr Pro Ser Ser Gly Asp Ser Ser Ser Pro Ala Gly Ala
                500                 505                 510
Pro Ser Pro Phe Asp Lys Glu Thr Glu Gly Gln Phe Tyr Asn Tyr Phe
    515                 520                 525
Pro Asn
    530
```